(12) United States Patent
Argento et al.

(10) Patent No.: US 10,987,214 B2
(45) Date of Patent: Apr. 27, 2021

(54) SURFACE TREATMENTS FOR ACCOMMODATING INTRAOCULAR LENSES AND ASSOCIATED METHODS AND DEVICES

(71) Applicant: Shifamed Holdings, LLC, Campbell, CA (US)

(72) Inventors: Claudio Argento, Felton, CA (US); Syed Hasan Askari, San Jose, CA (US); Arindam Datta, Hillsborough, NJ (US); Jacob Raquet, Elk Grove, CA (US); Tom Saul, Moss Beach, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 16/617,861

(22) PCT Filed: May 29, 2018

(86) PCT No.: PCT/US2018/034858
§ 371 (c)(1),
(2) Date: Nov. 27, 2019

(87) PCT Pub. No.: WO2018/222579
PCT Pub. Date: Dec. 6, 2018

(65) Prior Publication Data
US 2020/0121447 A1    Apr. 23, 2020

Related U.S. Application Data

(60) Provisional application No. 62/512,536, filed on May 30, 2017, provisional application No. 62/560,527, filed on Sep. 19, 2017.

(51) Int. Cl.
*A61F 2/16*    (2006.01)

(52) U.S. Cl.
CPC .... *A61F 2/1613* (2013.01); *A61F 2250/0056* (2013.01); *A61F 2310/00389* (2013.01)

(58) Field of Classification Search
CPC .... A61F 2/1613; A61F 2/1624; A61F 2/1635; A61F 2/1648; A61F 2220/005;
(Continued)

(56) References Cited

U.S. PATENT DOCUMENTS

| 4,440,918 A | 4/1984 | Rice et al. |
| 4,663,409 A | 5/1987 | Friends et al. |

(Continued)

FOREIGN PATENT DOCUMENTS

| AU | 2006200142 A1 | 7/2006 |
| AU | 2015361227 | 4/2017 |

(Continued)

OTHER PUBLICATIONS

Klank, et al. "CO2-laser micromachining and back-end processing for rapid production of PMMA-based microfluidic systems," Lab Chip, 2002, 2, 242-246, (Sep. 2002).
(Continued)

*Primary Examiner* — Paul B Prebilic
(74) *Attorney, Agent, or Firm* — Perkins Coie LLP

(57) ABSTRACT

An accommodating intraocular lens (AIOL) for implantation within a capsular bag of a patient's eye comprises first and second components coupled together to define an inner fluid chamber and an outer fluid chamber. The inner region of the AIOL provides optical power with one or more of the shaped fluid within the inner fluid chamber or the shape of the first or second components. A surface treatment or coating may be applied to one or more surfaces of the first and second components. The surface treatment is expected to decrease the roughness of the machined surfaces of the boundary surfaces of the first and second components, and (Continued)

thereby reduce the mass of water coalescing at such boundary surfaces. The disclosed surface treatments are also expected to increase the hydrophobicity (i.e., decrease the surface energy) of the corresponding surface(s), thereby decreasing the "wettability" of these surfaces.

17 Claims, 5 Drawing Sheets

(58) Field of Classification Search
 CPC ...... A61F 2220/0058; A61F 2250/0009; A61F 2250/001; A61F 2250/0013; A61F 2250/0036; A61F 2250/0056; A61F 2250/0091
 See application file for complete search history.

(56) References Cited

U.S. PATENT DOCUMENTS

| | | |
|---|---|---|
| 4,709,996 A | 12/1987 | Michelson et al. |
| 4,731,078 A | 3/1988 | Stoy et al. |
| 4,731,080 A | 3/1988 | Galin |
| 4,842,601 A | 6/1989 | Smith et al. |
| 4,892,543 A | 1/1990 | Turley |
| 4,932,966 A | 6/1990 | McMaster et al. |
| 5,074,942 A | 12/1991 | Orlosky et al. |
| 5,211,662 A | 5/1993 | Barrett et al. |
| 5,217,491 A | 6/1993 | Vanderbilt |
| 5,405,386 A | 4/1995 | Rheinish et al. |
| 5,423,929 A | 6/1995 | Grisoni et al. |
| 5,489,302 A | 2/1996 | Skottun |
| 5,556,929 A | 9/1996 | Yokoyama et al. |
| 5,612,391 A | 3/1997 | Chabrecek et al. |
| 5,620,720 A | 4/1997 | Glick et al. |
| 5,807,944 A | 9/1998 | Hirt et al. |
| 5,891,931 A | 4/1999 | Leboeuf et al. |
| 5,914,355 A | 6/1999 | Kuenzler |
| 5,944,753 A | 8/1999 | Galin et al. |
| 5,945,465 A | 8/1999 | Ozark et al. |
| 5,945,498 A | 8/1999 | Lohmann et al. |
| 6,140,438 A | 10/2000 | Kawaguchi et al. |
| 6,346,594 B1 | 2/2002 | Watanabe et al. |
| 6,447,920 B1 | 9/2002 | Chabrecek et al. |
| 6,465,056 B1 | 10/2002 | Chabrecek et al. |
| 6,521,352 B1 | 2/2003 | Lohmann et al. |
| 6,537,316 B1 | 3/2003 | Chambers |
| 6,558,420 B2 | 5/2003 | Green et al. |
| 6,582,754 B1 | 6/2003 | Pasic et al. |
| 6,586,038 B1 | 7/2003 | Chabrecek et al. |
| 6,630,243 B2 | 10/2003 | Ozark et al. |
| 6,660,035 B1 | 12/2003 | Yaross et al. |
| 6,685,741 B2 | 2/2004 | Landreville et al. |
| 6,713,583 B2 | 3/2004 | Liao et al. |
| 6,730,123 B1 | 5/2004 | Klopotek et al. |
| 6,734,321 B2 | 5/2004 | Chabrecek et al. |
| 6,747,090 B2 | 6/2004 | Haitjema et al. |
| 6,761,737 B2 | 7/2004 | Ting et al. |
| 6,764,511 B2 | 7/2004 | Ting et al. |
| 6,767,363 B1 | 7/2004 | Green et al. |
| 6,767,979 B1 | 7/2004 | Muir et al. |
| 6,786,934 B2 | 9/2004 | Ting et al. |
| 6,818,017 B1 | 11/2004 | Shu et al. |
| 6,818,158 B2 | 11/2004 | Pham et al. |
| 6,835,410 B2 | 12/2004 | Chabrecek et al. |
| 6,846,326 B2 | 1/2005 | Nguyen et al. |
| 6,858,040 B2 | 2/2005 | Ting et al. |
| 6,884,261 B2 | 4/2005 | Zadno-Azizi et al. |
| 6,893,595 B1 | 5/2005 | Muir et al. |
| 6,893,685 B2 | 5/2005 | Pasic et al. |
| 6,899,732 B2 | 5/2005 | Zadno-Azizi et al. |
| 6,935,743 B2 | 8/2005 | Shadduck |
| 6,969,403 B2 | 11/2005 | Yang et al. |
| 7,041,134 B2 | 5/2006 | Ting et al. |
| 7,087,080 B2 | 8/2006 | Ting et al. |
| 7,118,596 B2 | 10/2006 | Ting et al. |
| 7,198,640 B2 | 4/2007 | Nguyen |
| 7,217,778 B2 | 5/2007 | Flipsen et al. |
| 7,226,478 B2 | 6/2007 | Ting et al. |
| 7,416,562 B2 | 8/2008 | Gross et al. |
| 7,438,723 B2 | 10/2008 | Esch |
| 7,452,378 B2 | 11/2008 | Ting et al. |
| 7,468,397 B2 | 12/2008 | Schorzman et al. |
| 7,479,530 B2 | 1/2009 | Chan et al. |
| 7,557,231 B2 | 7/2009 | Schorzman et al. |
| 7,588,334 B2 | 9/2009 | Matsushita et al. |
| 7,591,849 B2 | 9/2009 | Richardson et al. |
| 7,601,766 B2 | 10/2009 | Schorzman et al. |
| 7,637,947 B2 | 12/2009 | Scholl et al. |
| 7,714,090 B2 | 5/2010 | Iwamoto et al. |
| 7,744,603 B2 | 6/2010 | Zadno-Azizi et al. |
| 7,744,646 B2 | 6/2010 | Zadno-Azizi et al. |
| 7,781,558 B2 | 8/2010 | Schorzman et al. |
| 7,806,929 B2 | 10/2010 | Brown et al. |
| 7,806,930 B2 | 10/2010 | Brown et al. |
| 7,842,087 B2 | 11/2010 | Ben |
| 7,883,540 B2 | 2/2011 | Niwa et al. |
| 7,906,563 B2 | 3/2011 | Huang et al. |
| 7,942,929 B2 | 5/2011 | Linhardt et al. |
| 8,003,710 B2 | 8/2011 | Medina et al. |
| 8,025,823 B2 | 9/2011 | Figueroa et al. |
| 8,034,107 B2 | 10/2011 | Stenger et al. |
| 8,048,155 B2 | 11/2011 | Shadduck et al. |
| 8,071,703 B2 | 12/2011 | Zhou et al. |
| 8,105,623 B2 | 1/2012 | Schorzman et al. |
| 8,158,712 B2 | 4/2012 | Your |
| 8,187,325 B2 | 5/2012 | Zadno-Azizi et al. |
| 8,211,955 B2 | 7/2012 | Chang et al. |
| 8,222,360 B2 | 7/2012 | Liao |
| 8,251,509 B2 | 8/2012 | Zickler et al. |
| 8,283,429 B2 | 10/2012 | Zhou et al. |
| 8,328,869 B2 | 12/2012 | Burns et al. |
| 8,357,771 B2 | 1/2013 | Medina et al. |
| 8,377,123 B2 | 2/2013 | Zadno et al. |
| 8,414,646 B2 | 4/2013 | Gifford et al. |
| 8,420,711 B2 | 4/2013 | Awasthi et al. |
| 8,425,595 B2 | 4/2013 | Evans et al. |
| 8,425,599 B2 | 4/2013 | Shadduck et al. |
| 8,425,926 B2 | 4/2013 | Qiu et al. |
| 8,430,928 B2 | 4/2013 | Liao |
| 8,454,688 B2 | 6/2013 | Evans et al. |
| 8,486,142 B2 | 7/2013 | Bumbalough et al. |
| 8,500,806 B1 | 8/2013 | Phillips et al. |
| 8,585,758 B2 | 11/2013 | Woods |
| 8,603,166 B2 | 12/2013 | Park |
| 8,609,745 B2 | 12/2013 | Medina et al. |
| 8,663,510 B2 | 3/2014 | Graney et al. |
| 8,680,172 B2 | 3/2014 | Liao |
| 8,728,158 B2 | 5/2014 | Whitsett |
| 8,759,414 B2 | 6/2014 | Winter et al. |
| 8,784,485 B2 | 7/2014 | Evans et al. |
| 8,827,447 B2 | 9/2014 | Awasthi et al. |
| 8,835,525 B2 | 9/2014 | Chang et al. |
| 8,851,670 B2 | 10/2014 | Zickler et al. |
| 8,863,749 B2 | 10/2014 | Gooding et al. |
| 8,877,227 B2 | 11/2014 | Ravi |
| 8,899,745 B2 | 12/2014 | Domschke |
| 8,900,298 B2 | 12/2014 | Chazan et al. |
| 8,956,409 B2 | 2/2015 | Ben |
| 8,968,399 B2 | 3/2015 | Ghabra |
| 8,992,609 B2 | 3/2015 | Shadduck |
| 8,993,651 B2 | 3/2015 | Chang et al. |
| 9,005,492 B2 | 4/2015 | Chang et al. |
| 9,005,700 B2 | 4/2015 | Qiu et al. |
| 9,006,359 B2 | 4/2015 | Schultz et al. |
| 9,011,532 B2 | 4/2015 | Catlin et al. |
| 9,023,915 B2 | 5/2015 | Hu et al. |
| 9,034,035 B2 | 5/2015 | Assia et al. |
| 9,039,174 B2 | 5/2015 | Awasthi et al. |
| 9,044,302 B2 | 6/2015 | Gooding et al. |
| 9,052,439 B2 | 6/2015 | Samuel et al. |
| 9,052,440 B2 | 6/2015 | Chang et al. |
| 9,095,424 B2 | 8/2015 | Atkinson et al. |
| 9,097,840 B2 | 8/2015 | Chang et al. |

(56) References Cited

U.S. PATENT DOCUMENTS

| | | |
|---|---|---|
| 9,125,736 B2 | 9/2015 | Atkinson et al. |
| 9,186,244 B2 | 11/2015 | Rao et al. |
| 9,198,572 B2 | 12/2015 | Zickler et al. |
| 9,254,189 B2 | 2/2016 | Azar et al. |
| 9,265,604 B2 | 2/2016 | Woods |
| 9,280,000 B2 | 3/2016 | Simonov et al. |
| 9,289,287 B2 | 3/2016 | Atkinson et al. |
| 9,326,848 B2 | 5/2016 | Woods |
| 9,364,316 B1 | 6/2016 | Kahook et al. |
| 9,387,069 B2 | 7/2016 | Atkinson et al. |
| 9,398,949 B2 | 7/2016 | Werblin |
| 9,421,088 B1 | 8/2016 | Schieber et al. |
| 9,427,312 B2 | 8/2016 | Tai et al. |
| 9,456,895 B2 | 10/2016 | Shadduck et al. |
| 9,486,311 B2 | 11/2016 | Vaughan et al. |
| 9,498,326 B2 | 11/2016 | Tsai et al. |
| 9,603,703 B2 | 3/2017 | Bumbalough |
| 9,622,855 B2 | 4/2017 | Portney et al. |
| 9,636,213 B2 | 5/2017 | Brady |
| 9,655,775 B2 | 5/2017 | Boukhny et al. |
| 9,681,946 B2 | 6/2017 | Kahook et al. |
| 9,693,858 B2 | 7/2017 | Hildebrand et al. |
| 9,744,027 B2 | 8/2017 | Jansen |
| 9,795,473 B2 | 10/2017 | Smiley et al. |
| 9,907,881 B2 | 3/2018 | Terrisse |
| 1,019,501 A1 | 2/2019 | Salahieh et al. |
| 1,035,005 A1 | 7/2019 | Argento et al. |
| 1,052,635 A1 | 1/2020 | Silvestrini |
| 1,054,871 A1 | 2/2020 | Salahieh et al. |
| 10,709,549 B2 | 7/2020 | Argento et al. |
| 10,736,734 B2 | 8/2020 | Salahieh et al. |
| 2001/0037001 A1 | 11/2001 | Muller et al. |
| 2001/0056165 A1 | 12/2001 | Mentak et al. |
| 2002/0072795 A1 | 6/2002 | Green et al. |
| 2002/0086160 A1 | 7/2002 | Qiu et al. |
| 2002/0102415 A1 | 8/2002 | Valint, Jr. et al. |
| 2002/0103536 A1 | 8/2002 | Landreville et al. |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0138141 A1 | 9/2002 | Zadno-Azizi et al. |
| 2002/0173847 A1 | 11/2002 | Pham et al. |
| 2002/0197414 A1 | 12/2002 | Chabrecek et al. |
| 2003/0008063 A1 | 1/2003 | Chabrecek et al. |
| 2003/0074060 A1 | 4/2003 | Zadno-Azizi et al. |
| 2003/0074061 A1 | 4/2003 | Pham et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0100666 A1 | 5/2003 | DeGroot et al. |
| 2003/0158560 A1 | 8/2003 | Portney |
| 2003/0162929 A1 | 8/2003 | Verbruggen et al. |
| 2003/0224185 A1 | 12/2003 | Valint, Jr. et al. |
| 2004/0111152 A1 | 6/2004 | Kelman et al. |
| 2004/0166232 A1 | 8/2004 | Kunzler et al. |
| 2004/0169816 A1 | 9/2004 | Esch |
| 2004/0184158 A1 | 9/2004 | Shadduck |
| 2004/0230300 A1 | 11/2004 | Bandhauer et al. |
| 2005/0013842 A1 | 1/2005 | Qiu et al. |
| 2005/0049700 A1 | 3/2005 | Zadno-Azizi et al. |
| 2005/0055092 A1 | 3/2005 | Nguyen et al. |
| 2005/0149183 A1 | 7/2005 | Shadduck et al. |
| 2005/0153055 A1 | 7/2005 | Ammon et al. |
| 2005/0165410 A1 | 7/2005 | Zadno-Azizi et al. |
| 2005/0228120 A1 | 10/2005 | Hughes et al. |
| 2005/0228401 A1 | 10/2005 | Zadno-Azizi et al. |
| 2006/0069432 A1 | 3/2006 | Tran |
| 2006/0100701 A1 | 5/2006 | Esch et al. |
| 2006/0100703 A1 | 5/2006 | Evans et al. |
| 2006/0116765 A1 | 6/2006 | Blake et al. |
| 2006/0178741 A1 | 8/2006 | Zadno-Azizi et al. |
| 2006/0241752 A1 | 10/2006 | Israel |
| 2006/0259139 A1 | 11/2006 | Zadno-Azizi et al. |
| 2006/0271187 A1 | 11/2006 | Zadno-Azizi et al. |
| 2007/0027540 A1 | 2/2007 | Zadno-Azizi et al. |
| 2007/0050025 A1 | 3/2007 | Nguyen et al. |
| 2007/0088433 A1 | 4/2007 | Esch et al. |
| 2007/0092830 A1 | 4/2007 | Lai et al. |
| 2007/0106377 A1 | 5/2007 | Smith et al. |
| 2007/0108643 A1 | 5/2007 | Zadno-Azizi et al. |
| 2007/0122540 A1 | 5/2007 | Salamone et al. |
| 2007/0201138 A1 | 8/2007 | Lo et al. |
| 2007/0203317 A1 | 8/2007 | Verbruggen et al. |
| 2007/0213817 A1 | 9/2007 | Esch et al. |
| 2007/0232755 A1 | 10/2007 | Matsushita et al. |
| 2007/0269488 A1 | 11/2007 | Ravi et al. |
| 2008/0001318 A1 | 1/2008 | Schorzman et al. |
| 2008/0003259 A1 | 1/2008 | Salamone et al. |
| 2008/0003261 A1 | 1/2008 | Schorzman et al. |
| 2008/0015689 A1 | 1/2008 | Esch et al. |
| 2008/0027461 A1 | 1/2008 | Vaquero et al. |
| 2008/0046074 A1 | 2/2008 | Smith et al. |
| 2008/0076897 A1 | 3/2008 | Kunzler et al. |
| 2008/0139769 A1 | 6/2008 | Iwamoto et al. |
| 2008/0143958 A1 | 6/2008 | Medina et al. |
| 2008/0181931 A1 | 7/2008 | Qiu et al. |
| 2008/0234457 A1 | 9/2008 | Zhou et al. |
| 2008/0300680 A1 | 12/2008 | Joshua et al. |
| 2008/0314767 A1 | 12/2008 | Lai et al. |
| 2009/0043384 A1 | 2/2009 | Niwa et al. |
| 2009/0118739 A1 | 5/2009 | Kappelhof et al. |
| 2009/0143499 A1 | 6/2009 | Chang et al. |
| 2009/0168012 A1 | 7/2009 | Linhardt et al. |
| 2009/0170976 A1 | 7/2009 | Huang et al. |
| 2009/0171459 A1 | 7/2009 | Linhardt et al. |
| 2009/0232871 A1 | 9/2009 | Hitz et al. |
| 2009/0247661 A1 | 10/2009 | Müller-Lierheim et al. |
| 2009/0292355 A1 | 11/2009 | Boyd et al. |
| 2010/0119744 A1 | 5/2010 | Yokoyama et al. |
| 2010/0120938 A1 | 5/2010 | Phelan et al. |
| 2010/0120939 A1 | 5/2010 | Phelan et al. |
| 2010/0121444 A1 | 5/2010 | Ben et al. |
| 2010/0160482 A1 | 6/2010 | Nachbaur et al. |
| 2010/0179653 A1 | 7/2010 | Argento et al. |
| 2010/0211170 A1 | 8/2010 | Liao et al. |
| 2010/0228346 A1 | 9/2010 | Esch et al. |
| 2010/0239633 A1 | 9/2010 | Strome et al. |
| 2010/0324674 A1 | 12/2010 | Brown et al. |
| 2011/0009519 A1 | 1/2011 | Awasthi et al. |
| 2011/0046332 A1 | 2/2011 | Breiner et al. |
| 2011/0118379 A1 | 5/2011 | Tighe et al. |
| 2011/0118834 A1 | 5/2011 | Lo et al. |
| 2011/0133350 A1 | 6/2011 | Qiu et al. |
| 2011/0140292 A1 | 6/2011 | Chang et al. |
| 2011/0144228 A1 | 6/2011 | Ravi et al. |
| 2011/0269869 A1 | 11/2011 | Medina et al. |
| 2011/0282442 A1 | 11/2011 | Scholl et al. |
| 2011/0295368 A1 | 12/2011 | Betser et al. |
| 2012/0010321 A1 | 1/2012 | Chang et al. |
| 2012/0023869 A1 | 2/2012 | Samuel et al. |
| 2012/0033183 A1 | 2/2012 | Dai et al. |
| 2012/0041097 A1 | 2/2012 | Zhou et al. |
| 2012/0046743 A1 | 2/2012 | Pinchuk et al. |
| 2012/0063000 A1 | 3/2012 | Batchko et al. |
| 2012/0078363 A1 | 3/2012 | Lu |
| 2012/0078364 A1 | 3/2012 | Stenger |
| 2012/0088843 A1 | 4/2012 | Chang et al. |
| 2012/0088844 A1 | 4/2012 | Kuyu et al. |
| 2012/0088861 A1 | 4/2012 | Huang et al. |
| 2012/0115979 A1 | 5/2012 | Chang et al. |
| 2012/0147323 A1 | 6/2012 | Domschke et al. |
| 2012/0238857 A1 | 9/2012 | Wong et al. |
| 2012/0245684 A1 | 9/2012 | Liao et al. |
| 2012/0314183 A1 | 12/2012 | Nakamura et al. |
| 2012/0330415 A1 | 12/2012 | Callahan et al. |
| 2013/0013060 A1 | 1/2013 | Zadno-Azizi et al. |
| 2013/0053954 A1 | 2/2013 | Rao et al. |
| 2013/0095235 A1 | 4/2013 | Bothe et al. |
| 2013/0106007 A1 | 5/2013 | Medina et al. |
| 2013/0110234 A1 | 5/2013 | DeVita et al. |

(56) References Cited

U.S. PATENT DOCUMENTS

| | | | |
|---|---|---|---|
| 2013/0116781 A1 | 5/2013 | Ben et al. | |
| 2013/0150961 A1 | 6/2013 | Evans et al. | |
| 2013/0176628 A1* | 7/2013 | Batchko | G02B 26/005 359/665 |
| 2013/0197125 A1 | 8/2013 | Awasthi et al. | |
| 2013/0224309 A1 | 8/2013 | Qiu et al. | |
| 2013/0228943 A1 | 9/2013 | Qiu et al. | |
| 2013/0245756 A1 | 9/2013 | Liao et al. | |
| 2013/0289294 A1 | 10/2013 | Awasthi et al. | |
| 2013/0304203 A1 | 11/2013 | Beer | |
| 2013/0317607 A1* | 11/2013 | DeBoer | A61F 2/1635 623/6.13 |
| 2014/0055750 A1 | 2/2014 | Dai et al. | |
| 2014/0171539 A1 | 6/2014 | Chang et al. | |
| 2014/0171542 A1 | 6/2014 | Chang | |
| 2014/0178595 A1 | 6/2014 | Bothe et al. | |
| 2014/0180403 A1 | 6/2014 | Silvestrini et al. | |
| 2014/0180406 A1* | 6/2014 | Simpson | A61F 2/1635 623/6.13 |
| 2014/0180407 A1 | 6/2014 | Sohn et al. | |
| 2014/1080406 | 6/2014 | Simpson | |
| 2014/0228949 A1 | 8/2014 | Argento et al. | |
| 2014/0277439 A1 | 9/2014 | Hu et al. | |
| 2014/0309735 A1 | 10/2014 | Sohn et al. | |
| 2014/0316521 A1 | 10/2014 | McLeod et al. | |
| 2014/0350124 A1 | 11/2014 | Chang et al. | |
| 2014/0379079 A1 | 12/2014 | Ben | |
| 2015/0088149 A1 | 3/2015 | Auld | |
| 2015/0092155 A1 | 4/2015 | Chang et al. | |
| 2015/0105760 A1 | 4/2015 | Silvestrini et al. | |
| 2015/0152228 A1 | 6/2015 | Chang et al. | |
| 2015/0164321 A1 | 6/2015 | Weibel et al. | |
| 2015/0177417 A1 | 6/2015 | Goshima et al. | |
| 2015/0351901 A1 | 12/2015 | Chicevic et al. | |
| 2016/0000558 A1 | 1/2016 | Honigsbaum et al. | |
| 2016/0008126 A1 | 1/2016 | Vaughan et al. | |
| 2016/0030161 A1 | 2/2016 | Rao et al. | |
| 2016/0058553 A1 | 3/2016 | Salahieh et al. | |
| 2016/0074154 A1 | 3/2016 | Woods | |
| 2016/0100938 A1 | 4/2016 | Weeber et al. | |
| 2016/0128826 A1 | 5/2016 | Rao et al. | |
| 2016/0151150 A1 | 6/2016 | Sato | |
| 2016/0184091 A1 | 6/2016 | Burns et al. | |
| 2016/0184092 A1 | 6/2016 | Flaherty et al. | |
| 2016/0250020 A1 | 9/2016 | Schieber et al. | |
| 2016/0256265 A1 | 9/2016 | Borja et al. | |
| 2016/0262875 A1 | 9/2016 | Smiley et al. | |
| 2016/0278914 A1 | 9/2016 | Sato et al. | |
| 2016/0296320 A1 | 10/2016 | Humayun et al. | |
| 2016/0296662 A1 | 10/2016 | Dudic et al. | |
| 2016/0317286 A1 | 11/2016 | Rao et al. | |
| 2016/0317287 A1 | 11/2016 | Rao et al. | |
| 2016/0331587 A1 | 11/2016 | Ueno et al. | |
| 2017/0000602 A1 | 1/2017 | Sohn et al. | |
| 2017/0020662 A1 | 1/2017 | Shadduck | |
| 2017/0049561 A1 | 2/2017 | Smiley et al. | |
| 2017/0049562 A1 | 2/2017 | Argento et al. | |
| 2017/0119521 A1 | 5/2017 | Kahook et al. | |
| 2017/0258581 A1 | 9/2017 | Borja et al. | |
| 2017/0348094 A1 | 12/2017 | Sohn et al. | |
| 2018/0110613 A1 | 4/2018 | Wortz et al. | |
| 2018/0161152 A1 | 6/2018 | Argento et al. | |
| 2018/0177589 A1 | 6/2018 | Argento et al. | |
| 2019/0159890 A1 | 5/2019 | Salahieh et al. | |
| 2019/0274823 A1 | 9/2019 | Argento et al. | |
| 2020/0146813 A1 | 5/2020 | Argento et al. | |
| 2020/0306031 A1 | 10/2020 | Salahieh et al. | |

FOREIGN PATENT DOCUMENTS

| | | |
|---|---|---|
| AU | 2010203427 | 5/2017 |
| AU | 2012335677 | 6/2017 |
| AU | 2015258287 | 12/2017 |
| CA | 2973684 | 7/2016 |
| CA | 2974639 | 8/2016 |
| CA | 2987311 | 12/2016 |
| CA | 2752046 | 4/2017 |
| CA | 2829143 | 4/2017 |
| CN | 101351169 | 6/2007 |
| CN | 102271623 | 7/2010 |
| CN | 108472129 | 8/2018 |
| EP | 0604369 A1 | 6/1994 |
| EP | 0734269 A1 | 10/1996 |
| EP | 0784652 A1 | 7/1997 |
| EP | 0800511 A1 | 10/1997 |
| EP | 0820601 A1 | 1/1998 |
| EP | 0826158 A1 | 3/1998 |
| EP | 0898972 A2 | 3/1999 |
| EP | 0907668 A1 | 4/1999 |
| EP | 0930357 A1 | 7/1999 |
| EP | 0604369 B1 | 8/1999 |
| EP | 0826158 B1 | 9/1999 |
| EP | 0947856 A2 | 10/1999 |
| EP | 0820601 B1 | 12/1999 |
| EP | 0800511 B1 | 1/2000 |
| EP | 0989138 A2 | 3/2000 |
| EP | 1084428 A1 | 3/2001 |
| EP | 1088246 A1 | 4/2001 |
| EP | 1090313 A1 | 4/2001 |
| EP | 1095711 A2 | 5/2001 |
| EP | 1095965 A1 | 5/2001 |
| EP | 1095966 A2 | 5/2001 |
| EP | 1109853 A1 | 6/2001 |
| EP | 0907668 B1 | 9/2001 |
| EP | 1141054 A1 | 10/2001 |
| EP | 1187873 A1 | 3/2002 |
| EP | 1200019 A1 | 5/2002 |
| EP | 1227773 A1 | 8/2002 |
| EP | 1230041 A2 | 8/2002 |
| EP | 1266246 A1 | 12/2002 |
| EP | 0898972 B1 | 4/2003 |
| EP | 1341485 A1 | 9/2003 |
| EP | 1364663 A1 | 11/2003 |
| EP | 1095711 B1 | 1/2004 |
| EP | 1141054 B1 | 2/2004 |
| EP | 1395302 A1 | 3/2004 |
| EP | 1410074 A1 | 4/2004 |
| EP | 1266246 B1 | 6/2004 |
| EP | 1109853 B1 | 9/2004 |
| EP | 1187873 B1 | 9/2004 |
| EP | 1084428 B2 | 11/2004 |
| EP | 1472305 A1 | 11/2004 |
| EP | 1230041 B1 | 12/2004 |
| EP | 0989138 B1 | 2/2005 |
| EP | 1095965 B1 | 2/2005 |
| EP | 1395302 B1 | 2/2005 |
| EP | 1507811 A1 | 2/2005 |
| EP | 1524953 A2 | 4/2005 |
| EP | 1200019 B1 | 9/2005 |
| EP | 1095966 B1 | 1/2006 |
| EP | 1660153 A2 | 5/2006 |
| EP | 1353611 B1 | 9/2006 |
| EP | 1696975 A1 | 9/2006 |
| EP | 1341485 B1 | 11/2006 |
| EP | 1723933 A2 | 11/2006 |
| EP | 1723934 A2 | 11/2006 |
| EP | 1750157 A1 | 2/2007 |
| EP | 1088246 B1 | 11/2007 |
| EP | 1857477 A1 | 11/2007 |
| EP | 1227773 B1 | 1/2008 |
| EP | 1888660 A2 | 2/2008 |
| EP | 1890650 A2 | 2/2008 |
| EP | 1902737 A1 | 3/2008 |
| EP | 1723933 B1 | 11/2008 |
| EP | 2035050 A2 | 3/2009 |
| EP | 2035480 A1 | 3/2009 |
| EP | 2035486 A1 | 3/2009 |
| EP | 1723934 B1 | 6/2009 |
| EP | 2066732 A2 | 6/2009 |
| EP | 2077292 A1 | 7/2009 |
| EP | 2092376 A1 | 8/2009 |
| EP | 1648534 B1 | 9/2009 |
| EP | 2094193 A2 | 9/2009 |

(56) References Cited

FOREIGN PATENT DOCUMENTS

| | | |
|---|---|---|
| EP | 2109784 A1 | 10/2009 |
| EP | 2120789 A2 | 11/2009 |
| EP | 2126614 A2 | 12/2009 |
| EP | 2035480 B1 | 2/2010 |
| EP | 2170708 A2 | 4/2010 |
| EP | 2185589 A2 | 5/2010 |
| EP | 2231207 A1 | 9/2010 |
| EP | 1750157 B1 | 10/2010 |
| EP | 2235094 A1 | 10/2010 |
| EP | 2276513 A2 | 1/2011 |
| EP | 2292672 A2 | 3/2011 |
| EP | 2356170 A1 | 8/2011 |
| EP | 2356497 A2 | 8/2011 |
| EP | 2109784 B1 | 10/2011 |
| EP | 2396355 A2 | 12/2011 |
| EP | 2035486 B1 | 4/2012 |
| EP | 2452212 A2 | 5/2012 |
| EP | 1857477 B1 | 6/2012 |
| EP | 1410074 B1 | 10/2012 |
| EP | 2092376 B1 | 10/2012 |
| EP | 2510051 A1 | 10/2012 |
| EP | 2513711 A1 | 10/2012 |
| EP | 2514791 A1 | 10/2012 |
| EP | 2356170 B1 | 12/2012 |
| EP | 2538266 A1 | 12/2012 |
| EP | 2563275 A1 | 3/2013 |
| EP | 2597113 A1 | 5/2013 |
| EP | 2598936 A1 | 6/2013 |
| EP | 2077292 B1 | 8/2013 |
| EP | 2625216 A1 | 8/2013 |
| EP | 2625217 A1 | 8/2013 |
| EP | 2625218 A1 | 8/2013 |
| EP | 2652532 A1 | 10/2013 |
| EP | 1830898 B1 | 3/2014 |
| EP | 2766750 A1 | 8/2014 |
| EP | 2452212 B1 | 3/2015 |
| EP | 2934383 A1 | 10/2015 |
| EP | 2200536 B1 | 1/2016 |
| EP | 2976042 A1 | 1/2016 |
| EP | 3185818 | 3/2016 |
| EP | 2129331 B1 | 4/2016 |
| EP | 3003217 A1 | 4/2016 |
| EP | 3025678 A1 | 6/2016 |
| EP | 2259750 B1 | 7/2016 |
| EP | 2934383 A4 | 7/2016 |
| EP | 3062741 A1 | 9/2016 |
| EP | 3072476 A1 | 9/2016 |
| EP | 1999188 B1 | 11/2016 |
| EP | 2685935 B1 | 11/2016 |
| EP | 2094193 | 1/2017 |
| EP | 2683287 | 2/2017 |
| EP | 3062742 | 2/2017 |
| EP | 3157466 | 4/2017 |
| EP | 3160404 | 5/2017 |
| EP | 3160683 | 5/2017 |
| EP | 3049023 | 6/2017 |
| EP | 3174500 | 6/2017 |
| EP | 3181094 | 6/2017 |
| EP | 2539351 | 7/2017 |
| ES | 2283058 T3 | 10/2007 |
| FR | 2653325 A1 | 4/1991 |
| JP | 59-501897 | 11/1984 |
| JP | 01-223970 | 9/1989 |
| JP | 2006-518222 | 8/2006 |
| JP | 2007-506516 | 3/2007 |
| JP | 2007-517616 | 7/2007 |
| JP | 2010-517639 | 5/2010 |
| JP | 2012-532685 | 12/2012 |
| WO | 9007545 A2 | 7/1990 |
| WO | 9007575 A1 | 7/1990 |
| WO | 9516475 A1 | 6/1995 |
| WO | 9611235 A1 | 4/1996 |
| WO | 9620919 A1 | 7/1996 |
| WO | 9631791 A1 | 10/1996 |
| WO | 9636890 A1 | 11/1996 |
| WO | 9749740 A1 | 12/1997 |
| WO | 9917684 A1 | 4/1999 |
| WO | 9929818 A1 | 6/1999 |
| WO | 9957581 A1 | 11/1999 |
| WO | 9960428 A1 | 11/1999 |
| WO | 9963366 A1 | 12/1999 |
| WO | 2000004078 A1 | 1/2000 |
| WO | 2000026980 A1 | 6/2000 |
| WO | 2000071613 A1 | 11/2000 |
| WO | 2001008607 A1 | 2/2001 |
| WO | 2001030512 A2 | 5/2001 |
| WO | 2001034067 A1 | 5/2001 |
| WO | 2001071392 A1 | 9/2001 |
| WO | 2002047583 A1 | 6/2002 |
| WO | 2002094331 A1 | 11/2002 |
| WO | 2003009014 A1 | 1/2003 |
| WO | 2003066707 A1 | 8/2003 |
| WO | 2003097711 A1 | 11/2003 |
| WO | 2004010905 A2 | 2/2004 |
| WO | 2004046768 A2 | 6/2004 |
| WO | 2004052242 A1 | 6/2004 |
| WO | 2004053536 A2 | 6/2004 |
| WO | 2004054471 A2 | 7/2004 |
| WO | 2004058318 A1 | 7/2004 |
| WO | 2004072689 A2 | 8/2004 |
| WO | 2005023331 A2 | 3/2005 |
| WO | 2005065734 A1 | 7/2005 |
| WO | 2006047383 A2 | 5/2006 |
| WO | 2006103674 A2 | 10/2006 |
| WO | 2006126095 A2 | 11/2006 |
| WO | 2007005778 A2 | 1/2007 |
| WO | 2007047529 A2 | 4/2007 |
| WO | 2007047530 A2 | 4/2007 |
| WO | 2007050394 A1 | 5/2007 |
| WO | 2007064594 A2 | 6/2007 |
| WO | 2008005644 A1 | 1/2008 |
| WO | 2008005652 A1 | 1/2008 |
| WO | 2008005752 A2 | 1/2008 |
| WO | 2008024766 A1 | 2/2008 |
| WO | 2008039655 A2 | 4/2008 |
| WO | 2008076729 A1 | 6/2008 |
| WO | 2008077040 A2 | 6/2008 |
| WO | 2008082957 A2 | 7/2008 |
| WO | 2008094876 A1 | 8/2008 |
| WO | 2008103798 A2 | 8/2008 |
| WO | 2008107882 A2 | 9/2008 |
| WO | 2008116132 A2 | 9/2008 |
| WO | 2008151088 A2 | 12/2008 |
| WO | 2009002703 A2 | 12/2008 |
| WO | 2009002789 | 12/2008 |
| WO | 2009015161 A2 | 1/2009 |
| WO | 2009015226 A2 | 1/2009 |
| WO | 2009015234 A2 | 1/2009 |
| WO | 2009015240 A2 | 1/2009 |
| WO | 2009085755 A1 | 7/2009 |
| WO | 2009085756 A1 | 7/2009 |
| WO | 2009127844 A2 | 10/2009 |
| WO | 2010056686 A1 | 5/2010 |
| WO | 2010056687 A2 | 5/2010 |
| WO | 2010081093 A2 | 7/2010 |
| WO | 2010093823 A2 | 8/2010 |
| WO | 2011005937 A1 | 1/2011 |
| WO | 2011026068 A2 | 3/2011 |
| WO | 2011071790 A1 | 6/2011 |
| WO | 2011075377 A1 | 6/2011 |
| WO | 2011106435 A2 | 9/2011 |
| WO | 2012006616 A1 | 1/2012 |
| WO | 2012015639 A1 | 2/2012 |
| WO | 2012047961 A1 | 4/2012 |
| WO | 2012047964 A1 | 4/2012 |
| WO | 2012047969 A1 | 4/2012 |
| WO | 2012082704 A1 | 6/2012 |
| WO | 2012129407 A2 | 9/2012 |
| WO | 2012129419 | 9/2012 |
| WO | 2013055746 A1 | 4/2013 |
| WO | 2013059195 | 4/2013 |
| WO | 2013070924 A1 | 5/2013 |
| WO | 2013158942 A1 | 10/2013 |
| WO | 2013166068 A1 | 11/2013 |

(56) References Cited

FOREIGN PATENT DOCUMENTS

| | | |
|---|---|---|
| WO | 2014093751 A2 | 6/2014 |
| WO | 2014093764 A1 | 6/2014 |
| WO | 2014095690 A1 | 6/2014 |
| WO | 2014099630 A1 | 6/2014 |
| WO | 2014143926 A1 | 9/2014 |
| WO | 2014149462 A1 | 9/2014 |
| WO | 2014152017 A1 | 9/2014 |
| WO | 2015038620 A2 | 3/2015 |
| WO | 2015048279 A1 | 4/2015 |
| WO | 2015066502 A1 | 5/2015 |
| WO | 2015148673 A1 | 10/2015 |
| WO | 2016018932 A1 | 2/2016 |
| WO | 2016033217 A1 | 3/2016 |
| WO | 2016038470 A2 | 3/2016 |
| WO | 2016061233 A1 | 4/2016 |
| WO | 2016122805 A1 | 8/2016 |
| WO | 2016140708 A1 | 9/2016 |
| WO | 2016195095 A1 | 12/2016 |
| WO | 2016201351 A1 | 12/2016 |
| WO | 2017079449 | 5/2017 |
| WO | 2017079733 | 5/2017 |
| WO | 2017087358 | 5/2017 |
| WO | 2017208230 | 12/2017 |
| WO | 2017221196 | 12/2017 |
| WO | 2017223544 | 12/2017 |
| WO | 2018119408 | 6/2018 |
| WO | 2018222579 | 12/2018 |
| WO | 2018227014 | 12/2018 |

OTHER PUBLICATIONS

Tsao, et al. "Bonding of thermoplastic polymer microfluidics. Microfluid Nanofuild," 2009, 6:1-16, (published online: Nov. 13, 2008).

Liang et al., "Bionic intraocular lens with variable focus and integrated structure," Optical Engineering 2015, vol. 54, No. 10, Article No. 105106, Internal pp. 1-7, (Oct. 2015).

International Search Report and Written Opinion received for PCT Application No. PCT/US18/34858, filed May 29, 2018; Applicant: Shifamed Holdings, LLC; dated Sep. 17, 2018, 9 pages.

International Search Report and Written Opinion for PCT Application No. PCT/US2020/029131, filed Apr. 21, 2020, Applicant: Shifamed Holdings, LLC, dated Sep. 21, 2020, 15 pages.

International Search Report and Written Opinion for PCT Application No. PCT/US2020/041644, filed Jul. 10, 2020, Applicant: Shifamed Holdings, LLC, dated Oct. 27, 2020, 11 pages.

Umbrecht, et al. "Solvent assisted bonding of polymethylmethacrylate: characterization using the response surface methodology," Jan. 2008, pp. 1325-1328.

* cited by examiner

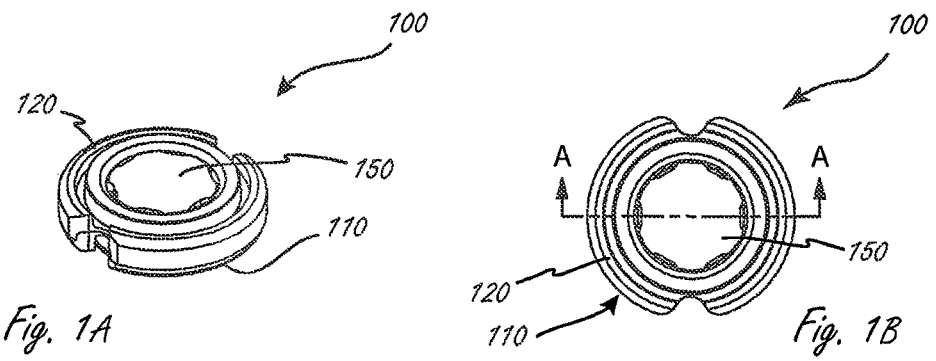
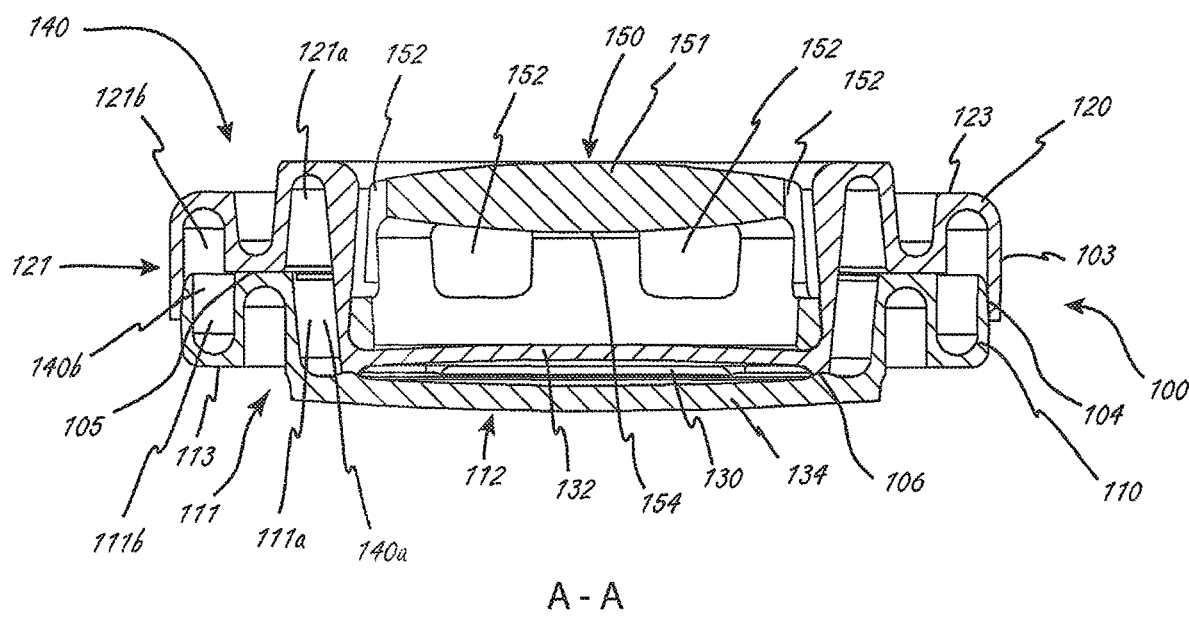

SURFACE TREATMENTS FOR ACCOMMODATING INTRAOCULAR LENSES AND ASSOCIATED METHODS AND DEVICES

CROSS-REFERENCE TO RELATED APPLICATION(S)

This application is a 35 U.S.C. § 371 U.S. National Phase application of International Patent Application No. PCT/US2018/034858, filed May 29, 2018, and entitled SURFACE TREATMENTS FOR ACCOMMODATING INTRAOCULAR LENSES AND ASSOCIATED METHODS AND DEVICES, which claims priority to U.S. Provisional Application Nos. 62/512,536, filed May 30, 2017, and titled SURFACE TREATMENTS FOR HYDROPHILIC AIOL, and 62/560,527, filed Sep. 19, 2017, and titled SURFACE TREATMENTS FOR HYDROPHILIC AIOL. The contents of each of the above applications are incorporated herein by reference in their entireties.

TECHNICAL FIELD

The present technology relates to medical devices and methods. In particular, embodiments of the present disclosure are directed to surface treatments for accommodating intraocular lenses (hereinafter "AIOLs" or "AIOL" for singular).

BACKGROUND

Cataracts can affect a large percentage of the worldwide adult population with clouding of the native crystalline lens and resulting loss of vision. Patients with cataracts can be treated by native lens removal and surgical implantation of a synthetic intraocular lens ("IOL"). Worldwide, there are millions of IOL implantation procedures performed annually. In the U.S., there are 3.5 million cataract procedures performed, while worldwide there are over 20 million annual procedures performed.

Although IOL implantation procedures can be effective at restoring vision, conventional IOLs have several drawbacks. For example, many prior IOLs are not able to change focus as a natural lens would (known as accommodation). Other drawbacks of conventional IOLs include refractive errors that occur after implantation and require glasses for correcting distance vision, or in other cases the IOLs can be effective in providing good far vision but patients need glasses for intermediate and near vision.

AIOLs have been proposed to provide accommodative optical power for patients. In particular, AIOLs for use in the replacement of the native lens, within the lens capsule, allow the brain to control the natural focusing of an external image on the retina of the eye in the native fashion. AIOLs typically comprise a central optical portion and a peripheral non-optical portion. The optical portion is used to focus the image on the retina within the eye and the non-optical structural portion provides the support structure to hold the optical portion in place and the focusing or accommodating control mechanism which interfaces to the lens capsule. Native accommodation results from changing the focal length of the lens (natural or artificial in this case) within the lens capsule by tightening or relaxing the ciliary muscles, which connect to the perimeter of the capsule via the zonules. Hence the brain, via a control feedback loop and action on the ciliary muscles, controls the optical power of the AIOL to accommodate the distance of the object being focused on the retina.

However, prior AIOLs are generally still in development and have different drawbacks. For example, prior AIOLs can provide insufficient accommodation after implantation or produce suboptimal refractive correction of the eye. The amount of accommodation of the prior AIOLs can also decrease after implantation in at least some instances. The prior AIOLs can also be too large to be inserted through a small incision of the eye and may require the incision to be somewhat larger than would be ideal. Also, at least some of the prior AIOLs can be unstable when placed in the eye, which can lead to incorrect accommodation and other errors. Many prior AIOLs are also susceptible to internal reflections associated with non-optical portions of the AIOL structure scattering into the optical field of view—referred to as dysphotopsia. For purposes of this disclosure, all such internal reflections will be termed "dysphotopsia."

Improved implantable intraocular lenses that accommodate with the natural mechanisms of controlling focusing of the eye that overcome at least some of the above deficiencies would be desirable. Ideally, such improved AIOLs would provide increased amounts of accommodation when implanted, provide refractive stability, introduce few if any perceptible visual artifacts, and allow the optical power of the eye to change from far vision to near vision in response to the distance of the object viewed by the patient.

SUMMARY

Embodiments of the present disclosure provide improved AIOLs and methods for making and using AIOLs. In many embodiments, the AIOLs include accommodating structure comprising a substantially hydrophilic outer structure and a substantially hydrophobic fluid interior. The hydrophilic structure is expected to provide a stable and very compliant structure capable of controlled deformation via minimal forces sustainable by the focusing mechanisms of the native lens.

The hydrophobic fluid provides a high refractive index while minimizing osmotic effects. The high refractive index providing good optical power. The substantially hydrophilic structural material is typically made or fabricated from copolymers of acrylics, copolymers of hydrophilic acrylics and hydrophobic acrylics, or other optically transparent polymeric material. The hydrophilicity of the material will vary as a function of the relative proportion of hydrophilic and hydrophobic monomers which have been polymerized to create the materials.

In many embodiments, the hydrophilic outer structure is comprised of components that are machined from the hydrophilic materials in a relatively dry form, assembled in the dry form, the structure hydrated after assembly, the refractive oil introduced after hydration.

The machining step may leave portions of the surface with different degrees of roughness and/or hydrophilicity.

The substantially hydrophobic fluid interior is comprised a hydrophobic oil chosen but not limited to any of silicone, copolymers of silicone and hydrocarbon oils.

When AIOL is placed in the capsule bag (implanted), following a conventional cataract surgery, the AIOL comprising the substantially hydrophilic outer structure and a substantially hydrophobic fluid interior prevents the water from coalescing at the boundary surface defined as the interface of the hydrophilic material and the hydrophobic fluid. In another embodiment, the AIOL comprising the substantially hydrophilic outer structure and a substantially hydrophobic fluid interior, retards the water from coalescing at the boundary surface defined as the interface of the hydrophilic material and the hydrophobic fluid. However, in some instances water may coalesce at the boundary surface. Without being bound by any particular theory, it is believed the likelihood of water coalescence can increase as a function of surface roughness or surface irregularities of the hydrophilic structure at the boundary of the hydrophobic fluid and hydrophilic structure. Similarly, without being bound by any particular theory, it is believed the likelihood of water coalescence can increase with changes in the equilibrium moisture content of the hydrated hydrophilic structure with changes in temperature. Such temperature changes can occur when the AIOL is placed from its storage at room temperature to the temperature existing in the eye. Again, without being bound by any particular theory, it is believed the likelihood of water coalescence can increase with changes in internal to external pressure.

Over time, such coalesced water may be forced out of the inner chamber into the hydrophilic structure. In one embodiment, this process will be enhanced by a positive pressure gradient from the interior to the outer environment. In another embodiment, as the AIOL equilibrates over time, the hydrophobic fluid pushes the water back from the boundary surface into the more compatible hydrophilic outer structure which is surrounded by the hydrophilic environment existing in the eye and thus acts as a sink for additional moisture diffusing out.

In one possible scenario, neighboring coalesced water may form an agglomerate or water drops that may take longer to be driven out of the interior or the boundary surface in a reasonable amount of time. Such water drops can also negatively affect optical quality of the AIOL. Further, in some instances, water may form into droplets at the surface. Additionally, in some instances, these droplets may comprise a micelle. In one embodiment of the present technology, the possibility of water drops coalescing within the fluid interior or at the interface of the hydrophilic material and the hydrophobic fluid is reduced by providing a surface treatment to increase the hydrophobicity (i.e., decrease the surface energy) of the boundary surfaces thereby decreasing the "wettability" of these surfaces. In some embodiments, the present technology is expected to reduce the possibility of water drops coalescing within the fluid interior or at the interface of the hydrophilic material and the hydrophobic fluid by providing a surface treatment to increase the hydrophobicity of the boundary surfaces thereby making it more compatible to the hydrophobic fluid. In further embodiments, the present technology is expected to reduce the possibility of water drops coalescing within the fluid interior or at the interface of the hydrophilic material and the hydrophobic fluid by application or addition of hydrophobic surface treatment or hydrophobic coating that can adhere to hydrophilic material to retard or minimize or block the moisture diffusion to the interface between the of the hydrophilic material and the hydrophobic fluid.

In some embodiments, surface treatments in accordance with the present technology modify a boundary volume of the hydrophilic structural material at and adjacent the boundary surface to some depth into the structural material. In such embodiments, the relative proportion of hydrophobic to hydrophilic molecules and/or end or pendant groups is increased within this boundary volume. For purposes of this disclosure, the terms "molecules" and "end or pendant groups" are used interchangeably.

In some such embodiments the proportion of hydrophobic molecules within the volume after treatment varies as a function of depth. In such embodiments the proportion of hydrophobic molecules is greatest at the boundary surface and decreases deeper into the structural material. Although such a distribution or gradient in concentration is not strictly a coating, for purposes of this disclosure, "coating" will be used to describe both a material lying on top of another, and the formation of a gradient in molecular distribution in material adjacent a coated surface, or a combination of both.

When choosing a coating material, it will be appreciated that depending up on the proportion of hydrophilic material to hydrophobic material, swelling of the coating can vary from swelling of the base material upon hydration of both materials. Such differential swelling may cause internal stresses, strains, and or delamination which may be detrimental to the function of the AIOL.

In many of the embodiments described herein a treatment comprises applying a coating material, which comprises a solution of monomers (and/or in some instances oligomers), crosslinkers, and a catalyst to initiate crosslinking of the monomers. Although the treatments described herein typically increase the hydrophobicity of the surfaces or materials, such treatments and coating materials may be modified such that the hydrophilicity may be increased.

In other aspects of the present technology, the same or similar surface treatments are applied to the interior surfaces of the AIOL device to minimize to reduce the surface roughness of the machined surfaces. In another aspect of the present technology, the same or similar surface treatments are applied to the exterior surfaces of the AIOL device to minimize the migration of proteins into the AIOL structure and or the attachment of cells to the outer surface of the AIOL structure.

In another application of the materials and methods described herein, coatings may be used to modify the reflective characteristics at or near the surfaces of the structures comprising the AIOL. Such materials and methods can provide for reductions and or elimination of light delivered to the retina which has been captured by and or transmitted through non-optical portions of the AIOL system and or result from multiple internal reflections. Such light often results from internal reflections associated with non-optical portions of the AIOL structure. Such treatments will reduce and or eliminate the occurrence of dysphotopsia resulting from such internal reflections associated with AIOL implantation.

BRIEF DESCRIPTION OF THE DRAWINGS

Features of the present technology are set forth with particularity in the appended claims. A better understanding of the features and advantages of the present technology will be obtained by reference to the following detailed description that sets forth illustrative embodiments, in which the principles of the invention are utilized, and the accompanying drawings of which:

FIG. 1A shows an isometric view of a fluid filled accommodating lens system comprising a bellows structure and a surface treatment configured in accordance with an embodiment of the present technology.

FIG. 1B shows a top view of the fluid filled accommodating lens system of FIG. 1A.

FIG. 1C shows a cross-sectional view of the fluid filled accommodating lens system of FIG. 1A taken along line A-A of FIG. 1B.

DETAILED DESCRIPTION

Figure 2A:
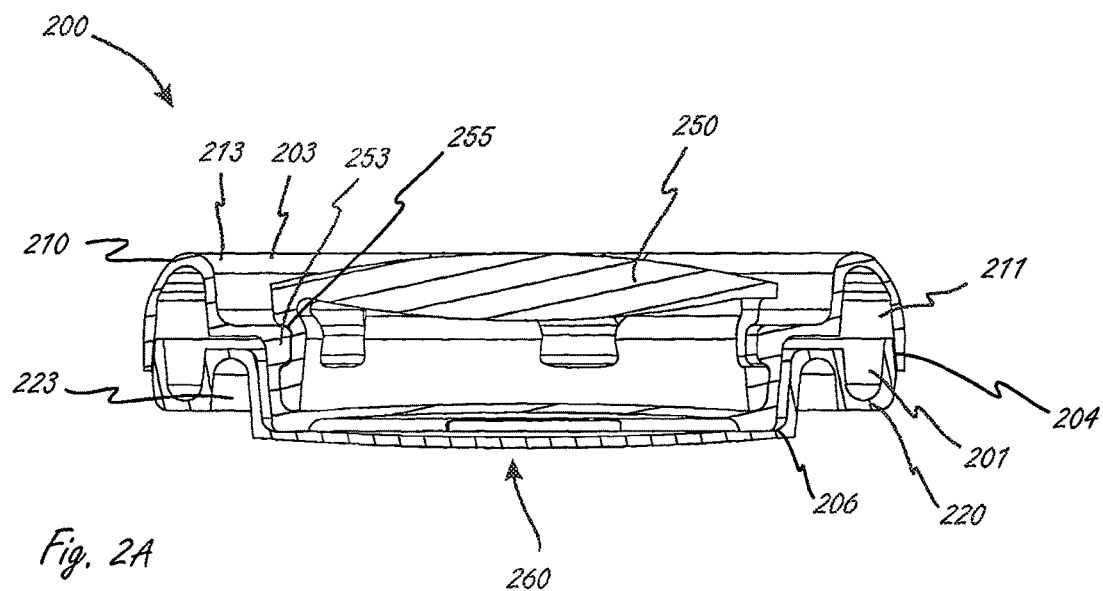
FIG. 2A shows a cross-sectional view of an alternate accommodating lens system configured in accordance with an embodiment of the present technology.

The present disclosure is directed to surface treatments for AIOLs and associated systems, methods, and devices. AIOLs, as described herein, are typically fabricated from dry hydrophilic components, which are hydrated prior to incorporating the substantially hydrophobic fluid interior into the assembly and the resulting assembly is kept in a hydrated state after manufacture. The surface treatments described herein will typically be applied to the dry pre-hydrated components or assemblies. In other embodiments, however, the surface treatments described herein may be applied to the components or assemblies in a fully hydrated state to take advantage of higher surface area (accessible in the hydrated state). In some instances, surfaces that are not to be treated can be masked. In other instances, the treatment may be applied without a mask.

AIOLs, as described herein, typically comprise a central optical structure comprised of at least one deformable optical component (e.g., an optical element) spaced apart along an optical axis, such as by a support structure concentric with the optical axis of the lenses. Several embodiments include a first optical component and a second optical component, and at least one of the first and second optical components can be deformable while the other of the first and second optical components can be deformable or rigid. The volume bounded by the first and second optical components, and optionally the lens support structure, may define a fluid chamber or fluid reservoir that can be filled with an ionic solution, such as saline, or non-ionic solutions such as dextran or silicone oil. In some embodiments of the AIOLs described herein, the AIOL components are machined from a dry pre-hydrated hydrophilic material. The machined components are then assembled such that the assembled AIOL comprises an outer surface, and an inner volume bounded by an inner surface. The inner volume is then filled by a hydrophobic optical fluid after the assembled device is hydrated. In some embodiments, the surface treatment is expected to decrease the roughness of the machined surfaces of the boundary surfaces and thereby reduce the mass of water coalescing at the boundary surface.

In other embodiments described herein, suitable coatings may be used to minimize dysphotopsia. Such coatings may comprise, for example, agents that minimize the amount of light transmitted through the coating. Transmission may be modified by increasing the scattering of light at the surface of the coating or within the coating, reflecting and or absorbing the light at the surface of or within the coating, or some combination. Such light interactions can be effected by the incorporation of particles within the coating material. A non-exhaustive list of a few such additive materials are opaque particles such as $TiO_2$, gas bubbles, and water-soluble (or other solvent soluble) particles such as sugars or salts.

The hydrophilic acrylics described herein may include copolymers of both hydrophilic and hydrophobic components. The following is a partial list of some such component materials: 2-Hydroxyethyl methacrylate (HEMA), 2-Ethoxyethyl methacrylate (EOEMA), Ethylene glycol dimethylacrylate (EGDMA), polymethyl methacrylate (PMMA), Butyl acrylate, Hexyl acrylate and Hexafluoroisopropyl acrylate.

One suitable hydrophilic copolymer acrylic from which AIOLs described herein may be fabricated is a copolymer of HEMA and EOEMA. Such a material is BENZ IOL 25 UVX which may be purchased from Benz Research & Development, 6447 Parkland Dr., Sarasota, Fla. 34243 United States.

In some embodiments, surface treatments are aimed at minimizing, retarding or preventing water coalescence, and will be applied to the boundary surfaces described as the interface of the hydrophilic material and the hydrophobic fluid.

Treatments applied to the exterior surfaces of the AIOL to minimize migration of organic molecules or proteins typically comprise a smaller increase in hydrophobicity or a smaller reduction in hydrophilicity or a smaller reduction in surface energy than those applied to the inner boundary surfaces of the chamber surrounding the substantially hydrophobic fluid.

The nature and amount of surface treatment applied in accordance with the present technology can be controlled. In one embodiment, for example, the surface treatments will slightly decrease the surface energy and slightly increase the surface hydrophobicity of the hydrophilic material. In another embodiment, the surface treatments will decrease the surface energy and increase the surface hydrophobicity of the hydrophilic material. In still another embodiment, the surface treatments will substantially decrease the surface energy and substantially increase the surface hydrophobicity of the hydrophilic material.

In some embodiments, hydrophobicity is achieved by treating the boundary surfaces, or portions of the boundary surfaces, with surface treatment agents which comprise a portion to affix to the hydrophilic material while presenting another hydrophobic portion to the interior of the chamber surrounding the substantially hydrophobic fluid. The hydrophobic portions applied to the boundary surfaces may have different chemical compositions and different degree of hydrophobicity than those applied to the interior of the chamber surrounding the substantially hydrophobic fluid.

In some such treatments, a molecule with a hydrophobic end group can be chemically affixed to the surface of interest such that the hydrophobic end group is presented to the exterior. Chemically affixed may include either covalently bonds, hydrogen bonds, or chemical crosslinking. In another such surface treatments, a hydrophobic molecule can be covalently bonded, chemically crosslinked, or adhered by hydrogen bonding to the surface of interest. For chemical cross-linking, biocompatible cross linkers such as amines, trifunctional or multifunctional hydroxyl compound, glycerin, acrylics and Ethylene glycol dimethacrylate [EGDMA] can be used.

The application area of the surface treatment can be continuous, semi-continuous or in separate patches. In an alternative treatment for use with copolymers comprised of hydrophilic and hydrophobic constituents, a surface treatment may be applied which preferentially etches the hydrophilic portions while leaving intact the hydrophobic portions.

In yet another alternative the surface treatment comprises applying a layer of copolymer to the surface of interest which has a much lower hydrophilicity or a much lower saturation water content than the AIOL assembly or outer structure material. Alternatively, or in combination, the surface treatment substantially covers the channels or passages in the outer structure material in order to prevent or resist the diffusion of moisture through the surface layer in the hydrated use state of the outer structure material. In some such embodiments, the copolymer may contain the same constituents as the hydrophilic base material being coated but in different proportions of hydrophilic acrylics and hydrophobic acrylics. In one embodiment, the surface treatment comprises at least 50% of the hydrophobic acrylics by weight. In another embodiment, the surface treatment comprises at least 70% of the hydrophobic acrylics by weight. In another embodiment, the surface treatment comprises at least 90% of the hydrophobic acrylics by weight. In some embodiments, the surface treatment comprises a thin coating of material of the same surface energy as the structure applied in such a fashion as to reduce the roughness of the surfaces resultant from the manufacturing processes.

The surface treatments can be delivered by various methods such as brush coating, spray coating, dip coating, vapor deposition, plasma deposition or their combinations thereof. In embodiments in which the coating material is delivered in a solvent, useful biocompatible solvents include but not limited to NMP, DMSO, TCE, ethyl acetate, THF, DMF and DMAC.

In one embodiment, the surface of interest may undergo one surface treatment. In another embodiment, the surface of interest may undergo two surface treatments. In yet another embodiment, the surface of interest may undergo more than two surface treatments.

In some instances, the surfaces to be treated will be prepared or pretreated by surface modifications or surface activation such as treatments by; UV exposure, plasma, corona discharge, alcohol etching solvent cleaning and acidic etching.

In some instances, the surfaces to be treated will be prepared by surface modifications or surface activation such as treatments which replace OH groups with other groups which render the surface less hydrophilic.

Materials comprised in the surface treatments may be selected from, but are not limited to, any of the following: Silicone, Polyurethane, and Acrylic.

In one embodiment, the silicone for the surface treatment comprises a linear silicone polymer. In another embodiment, the silicone for the surface treatment comprises a cross-linked silicone polymer.

In one embodiment, the polyurethane for the surface treatment comprises an aromatic hard segment. In another embodiment, the polyurethane for the surface treatment comprises an aliphatic hard segment. In still other embodiments, the polyurethane for the surface treatment may comprise hydrophobic polyurethanes such as polycarbonate polyurethane, poly(carbonate-co-siloxane) polyurethane, polysiloxane polyurethane, polyether polyurethane, poly(ether-co-carbonate) polyurethane, or poly(ether-co-siloxane), a linear urethane polymer, and/or a cross-linked urethane polymer.

In one embodiment, the acrylic comprises a hydrophobic acrylic. In another embodiment, the acrylic comprises a copolymer of hydrophilic acrylics and hydrophobic acrylics. Exemplary hydrophilic acrylics include but are not limited to 2-Hydroxyethyl methacrylate (HEMA). Exemplary hydrophobic acrylics include but are not limited to 2-Ethoxyethyl methacrylate (EOEMA), polymethyl methacrylate (PMMA), Butyl acrylate, Hexyl acrylate and Hexafluoroisopropyl acrylate. In one embodiment, the acrylic comprises a crosslinker. In one embodiment, the acrylic comprises a cross-linked acrylic polymer.

The average thickness of surface treatment is less than 20 micrometers, preferably less than 10 micrometers and more preferably less than 2 micrometers. The surface treatment is substantially chemical compatible with the hydrophilic outer structure leading to better adhesion with the hydrophilic outer structure. The surface treatment will not degrade or disintegrate in aqueous environment and is hydrolytically stable. The surface treatment is ductile and optically clear so it will not interfere with functioning of the AIOL. The surface treatment is biocompatible.

Several possible Acrylic-based recipes are presented in Table A and Table B below. Several more possible treatment material recipes and procedures are listed in the Examples below.

TABLE A

A selection of possible curing cycles (examples) for the acrylic materials listed in Table A are 4-18 hours at 60 C., 4-24 hours at 50 C., 10 hours at 30 C. and 5 hours 100 C.

| | Formula 1 | Formula 2 | Formula 3 | Formula 4 |
|---|---|---|---|---|
| (all by weight) | | | | |
| EOEMA family | | | | |
| 2-Ethoxyethyl methacrylate [EOEMA] | 30% | 60% | 99.63% | 97.02% |
| 2-Hydroxyethyl methacrylate [HEMA] | 69.63% | 39.63% | 0% | 0% |
| 2,2-azobis (2,4-dimethylvaleronitrile) | 0.07% | 0.07% | 0.07% | 0.068% |
| Ethylene glycol dimethacrylate [EGDMA] | 0.30% | 0.30% | 0.30% | 2.91% |
| FLUORO family | | | | |
| 1,1,1,3,3,3-Hexafluoroisopropyl acrylate | 63.19% | 62.79% | 58.49% | |
| Butyl acrylate | 36.44% | 32.02% | 0.00% | |
| Hexyl acrylate | 0.00% | 0.00% | 41.14% | |
| 4-Hydroxybutylacrylate | 0.00% | 4.81% | 0.00% | |
| Ethylene glycol dimethacrylate [EGDMA] | 0.30% | 0.30% | 0.30% | |
| 2,2-azobis (2,4-dimethylvaleronitrile) | 0.07% | 0.07% | 0.07% | |

EGDMA is a crosslinker
Azobis is a thermal and UV initiator

TABLE B

| Compound (all by weight) | 1% HEMA | 5% HEMA | 25% HEMA | 50% HEMA |
| --- | --- | --- | --- | --- |
| 2-Hydroxyethyl Methacrylate (HEMA) | 1.00% | 5.00% | 25.00% | 50.00% |
| 2-Ethoxyethyl Methacrylate (EOEMA) | 98.50% | 95.00% | 75.00% | 50.00% |
| Ethylene glycol dimethacrylate (EGDMA) | 0.30% | 0.30% | 0.30% | 0.30% |
| 2,2'-Azobis(2,4-dimethylvaleronitrile) | 0.07% | 0.07% | 0.07% | 0.07% |

Coatings described herein may be applied by any suitable means including, for example, painting, spraying, vapor deposition processes, and/or application via a mist chamber. One useful application method comprises subjecting the surface and adjacent volume of structural material to a volume of the unpolymerized formula or partially polymerized (comprised of oligomers) formula. The time between the application of the treatment and the initiation (or re-initiation) of polymerization, treatment time, may be varied for any of the treatment methods. The treatment time will affect the depth of penetration of the monomers and multimers comprising the coating material prior to polymerization. The volume of coating material will be greater closer to the application surface and decrease as the distance from the coating surface increases.

FIGS. 1A-1C illustrate various views of an AIOL 100 including a surface treatment configured in accordance with an embodiment of the present technology. Referring first to FIGS. 1A and 1B, for example, the AIOL 100 comprises three primary structures including (a) a fixed lens assembly 150, (b) a first component 110, and (c) a second component 120. The first component 110 is mated with and bonded to the second component 120. The fixed lens assembly 150 is held in place relative to the first and second components 110 and 120 via a mechanical interface and is not bonded in place.

FIG. 1C is a cross-sectional view of AIOL 100 taken along line A-A of FIG. 1B. As best seen in FIG. 1C, the first and second components 110 and 120 are bonded together at seams or bond joints 104, 105, and 106 to couple the first and second components 110 and 120 to one another. When bonded, an outer or peripheral portion 113 of the first component 110 and an outer or peripheral portion 123 of the second component 120 define an outer surface 103 of the AIOL 100.

The first component 110 includes a first inner surface 111 having one or more inner surface regions defining various portions of the first component 110. In the illustrated embodiment, for example, the first component 110 includes a first inner surface region 111a and a second inner surface region 111b. The second component 120 also comprises a second inner surface 121 having one or more inner surface regions defining various portions of the second component. For example, the second component 120 includes a third inner surface region 121a and a fourth inner surface regions 121b. In the embodiment shown in FIG. 1C, the first inner surface region 111a (of the first component 110) and the third inner surface region 121a (of the second component 120) define, at least in part, a first bellows region 140a. Similarly, the second inner surface region 111b (of the first component 110) and the fourth inner surface region 121b (of the second component 120) define, at least in part, a second bellows region 140b (collectively, bellows region 140).

The AIOL 100 has a fluid accommodating lens 112 defined by a fluid chamber or reservoir 130 bounded between a first optical component 132 and a second optical component 134. The first and second optical components 132 and 134 may be planar members (e.g., optical membranes) of the first and second components 110 and 120, respectively. The first and second optical components 132 and 134, for example, can be integrally formed as optical membranes with the other portions of the first and second components 110 and 120. In alternate embodiments, either or both of the membranes of the first and second optical components 132 and 134 may be a lens (i.e., have an optical power).

The fluid chamber 130 is in fluid communication with the bellows region 140 to transfer fluid (e.g., the hydrophobic fluid) between the fluid chamber 130 and the bellows region 140 in response to shape changes of the lens capsule to provide optical power changes to the accommodating intraocular lens. In some embodiments, for example, the fluid chamber 130 and the bellows region 140 may be filled with a substantially hydrophobic fluid that is transferred therebetween.

Referring to FIGS. 1A and 1C together, the fixed lens assembly 150 includes an optical portion 151 and passages 152. The optical portion 151 has a fixed power that may comprise an asymmetrically powered lens or other suitable lens, and the passages 152 are holes, slots, orifices, etc., that pass through and extend through a portion of the fixed lens assembly 150, but not the optical portion 151. The fixed lens assembly 150 further includes an inner surface 154 facing and adjacent to an engagement surface of the first component 110 and/or second component 120 to which the fixed lens assembly 150 is coupled.

As noted previously, the AIOL 100 may include a surface treatment on various portions of one or more components of the AIOL 100. In some embodiments, for example, portions of inner surfaces 111 and 121 surrounding the bellows region 140 may be treated to reduce the surface energy or increase the surface hydrophobicity. In some embodiments, some or all of the mating surfaces are left untreated. In alternate embodiments, all of inner surfaces (including inner surfaces 111 and 121) are treated to reduce their surface energy or increase the surface hydrophobicity.

In some embodiments, only selected portions of inner surfaces 111 and 121 are treated to reduce, prevent or resist the diffusion of moisture through the surface layer. In alternate embodiments, all or substantially all of inner surfaces 111 and 121 are treated to resist the diffusion of moisture through the surface layer in the hydrated use state of the outer structure material.

In some embodiments, only the portions of outer surface 113 surrounding the fluid accommodating region 112 may be treated to reduce the surface energy and/or reduce prevent or resist the diffusion of moisture through the surface layer. In alternate embodiments, all of outer surfaces 113 and 123 can be treated to reduce their surface energy, reduce the pore size of the surface layer, and/or increase the surface hydrophobicity.

In some embodiments, a surface treatment that resists the diffusion of moisture through the surface comprises substantially covering the channels or passages in the outer structure material of the AIOL 100 to prevent or resists the diffusion of moisture through the surface.

Suitable surface treatments for use with the AIOL 100 of FIGS. 1A-1C and other AIOLs configured in accordance with the present technology utilize a variation of Formula 4 of the EOEMA family listed in Table A provided above. In such embodiments, the inner machined surfaces of the first and second components 110 and 120 of AIOL 100 (FIGS. 1A-1C) may be treated in a dry state prior to assembly by spraying the coating material. In some embodiments, some combination of the surfaces comprising bond joints 104, 105, 106 can be masked during the coating process.

In an alternate procedure, the first and second components 110 and 120 can be filled with a coating material and the coating material is allowed to diffuse into the structural material for a period of time between 1 minute 1 day, more preferably between 5 minutes and 20 minutes prior to the initiation of polymerization. In certain embodiments, selected surfaces of the first component 110 and second component 120 (e.g., the bond joints 104, 105, 106 and/or other selected surfaces) may be masked.

Figures 2B, 2C:
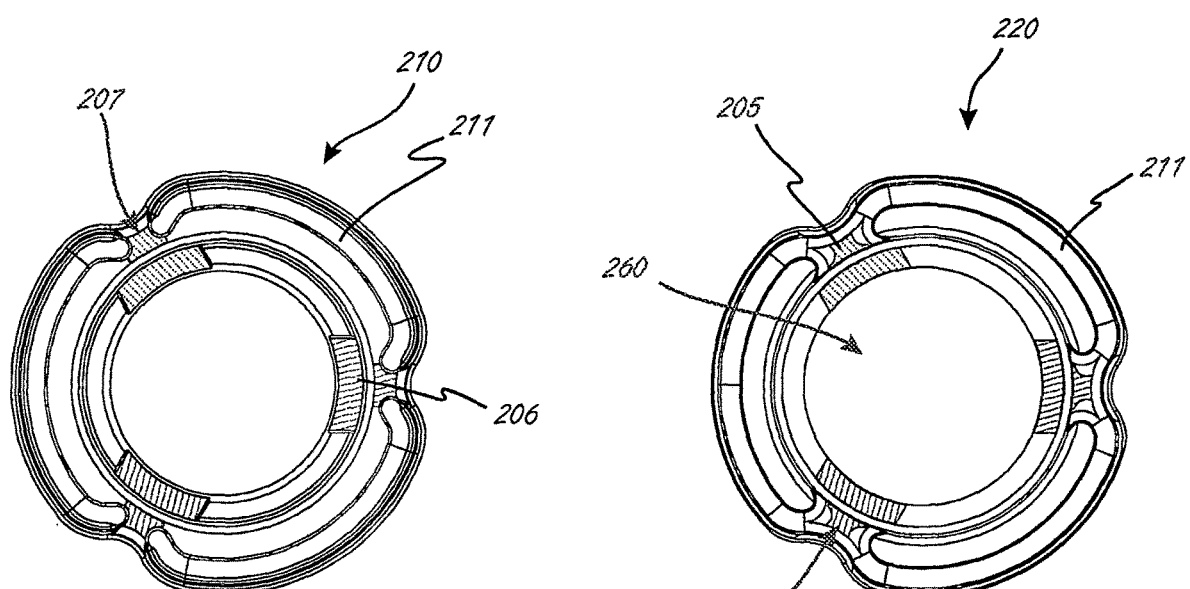
FIG. 2B and FIG. 2C illustrate top views of a first component and a second component, respectively, of an accommodating lens system configured in accordance with an embodiment of the present technology.

FIGS. 2A, 2B, and 2C illustrate an AIOL 200 configured in accordance with another embodiment of the present technology. The AIOL 200 is similar to embodiments of the AIOL 100 described above with reference to FIGS. 1A-1C. For example, the AIOL 200 comprises three primary structures including (a) a fixed lens assembly 250, (b) a first component 210, and (c) a second component 220. The first and second components 210 and 220 are bonded together at seams or bond joints 204, 205, and 206 to couple the first and second components 210 and 220 to one another. After bonding, an outer or peripheral portion 213 of the first component 210 and an outer or peripheral portion 223 of the second component 220 define an outer surface 203 of the AIOL 200. The AIOL 200 further includes an inner surface 211.

As best seen in FIG. 2A, the fixed lens assembly 250 can be engaged to and aligned with a fluid accommodating lens 260 of the AIOL 200 by engaging a continuous thickened region 253 of the first component 210 with an engagement feature 255 of the fixed lens assembly 250.

FIGS. 2B and 2C are top views of the first component 210 and second component 220, respectively, before being joined together. As best seen in FIGS. 2B and 2C, certain portions of the AIOL 200 may be masked before/during a surface treatment or coating process. Such masked regions 207 are typically regions where the first component 210 and the second component 220 are bonded together—including, for example, seams/bond joints 204 (FIG. 2A), 205 (FIG. 2C), and 206. Many suitable bonding agents are designed for hydrophilic base materials. Accordingly, masking the selected regions before the surface treatment or coating process will ensure that such regions are not subjected to the surface treatment, and thereby allow the masked regions to provide enhanced bonding between the first and second components 210 and 220. It will be appreciated that in other embodiments additional regions or different regions of the first component 210 and/or second component 220 may be masked before surface treatment. Further, in some embodiments no masking may be used during surface treatment or coating.

Figure 3A:
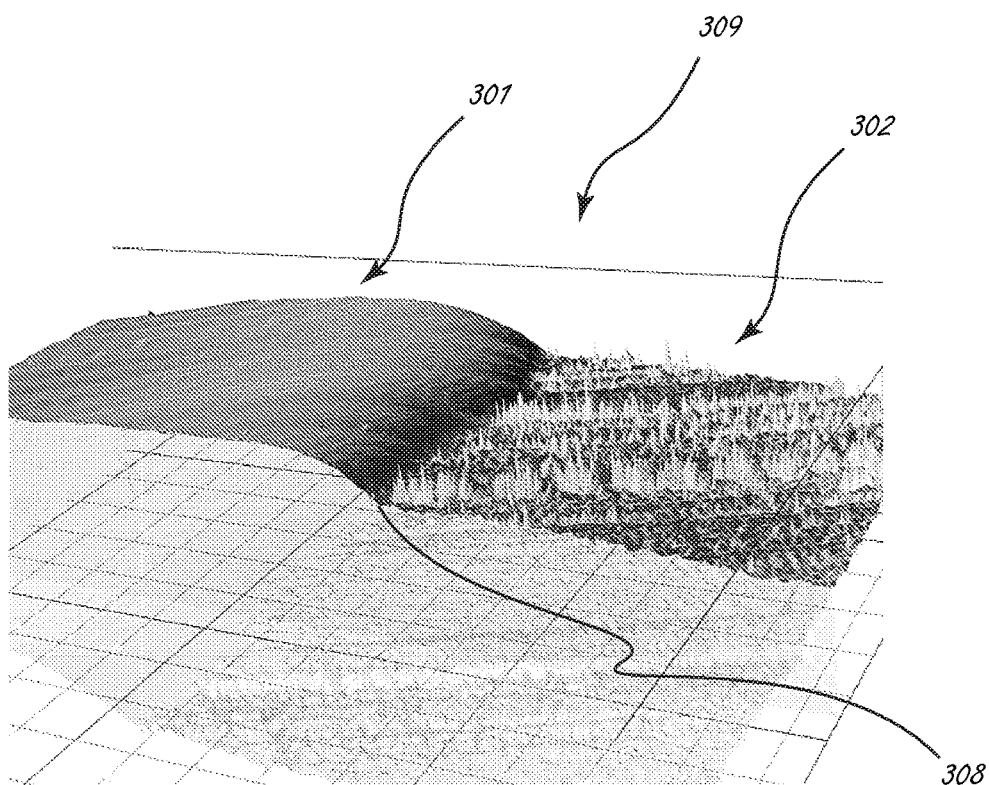
FIG. 3A illustrates a laser profilometery image of a portion of a machined surface of an accommodating lens system configured in accordance with an embodiment of the present technology.
Figure 3B:
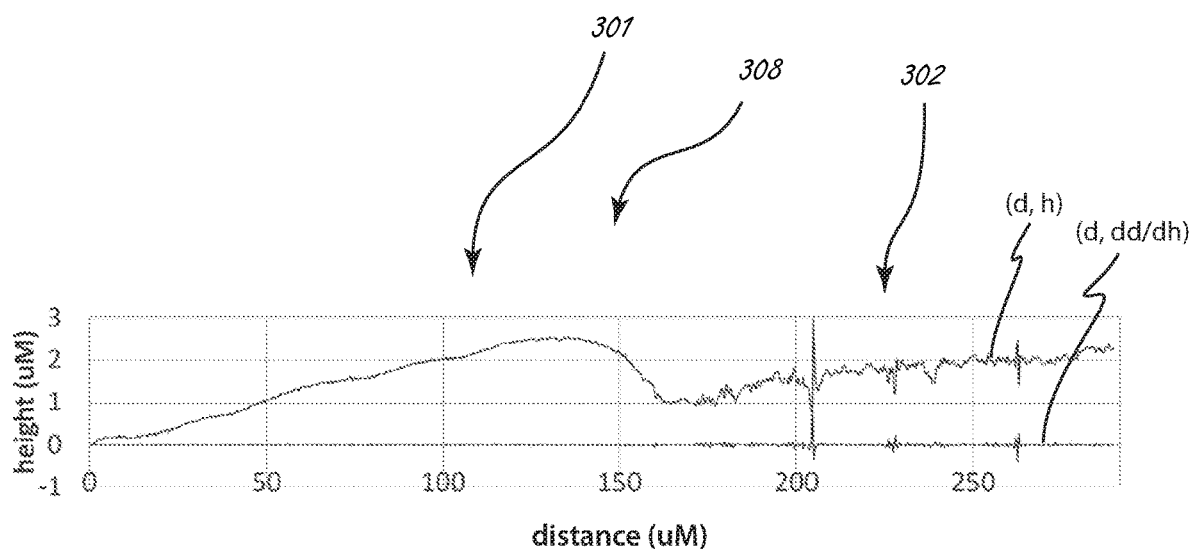
FIG. 3B is a display diagram illustrating a profile of a portion of a machined surface of an accommodating lens system.

FIG. 3A illustrates a laser profilometery image of a portion of a machined surface 309 of the BENZ material. On the left side of the drawing is a coated surface 301 and on the right side of the drawing is an uncoated surface 302. Element 308 illustrates an arbitrary cross section of the surface. FIG. 3B is a graphic representation of the profile 308 as a function of distance and height (d, h) and its first derivative (d, dh/dd). As can be seen both in the surface illustration of FIG. 3A and the cross-section illustration of FIG. 3B, a surface treatment or coating reduces surface roughness. In particular, the first derivative of the profile on the coated portion can be seen to fall within a relatively small range while the first derivative on the profile on the uncoated region varies dramatically.

Figure 4A:
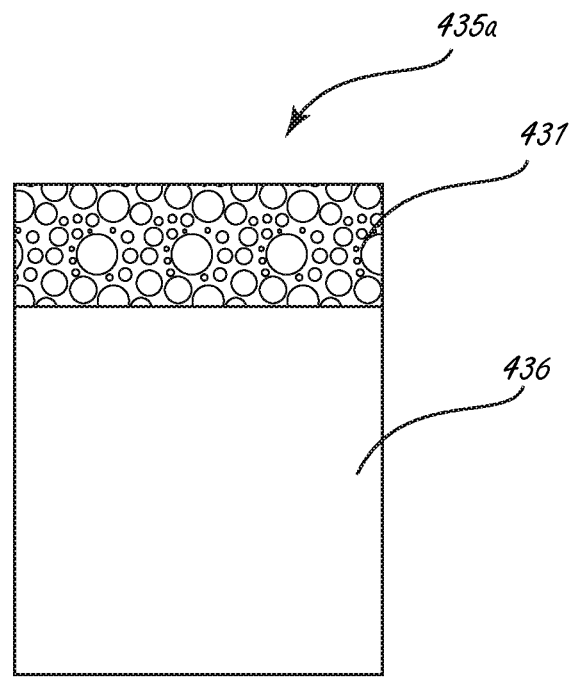
FIGS. 4A and 4B illustrate a section of a hydrophilic accommodating lens structure including a base layer and a light attenuating layer or coating layer in accordance with an embodiment of the present technology.
Figure 4B:
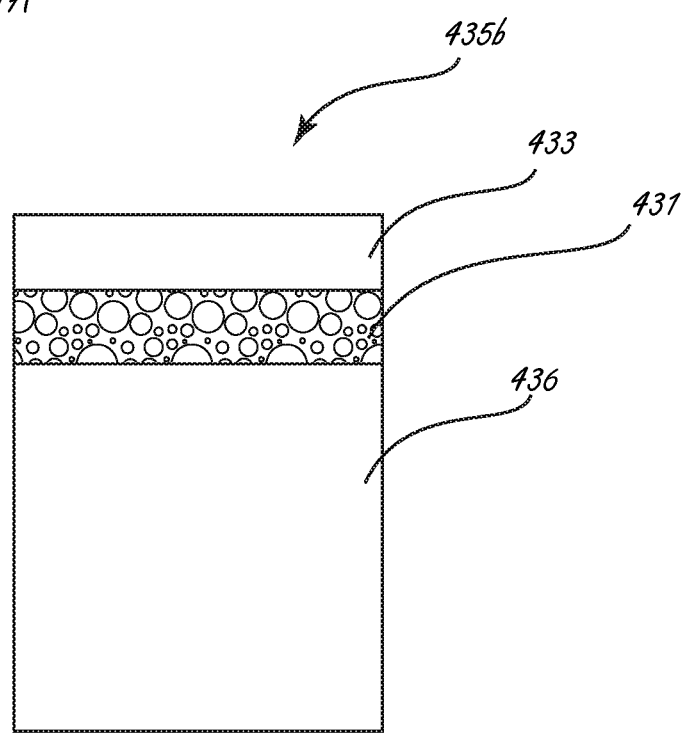

FIG. 4A illustrates a section of a hydrophilic AIOL structure 435a comprising a base layer 436 and a light attenuating layer or coating layer 431. The light attenuating layer 431 is rendered less transparent by means of any of the techniques discussed herein. FIG. 4B illustrates another arrangement of a section of a hydrophilic AIOL structure 435b comprising the base layer 436 with the light attenuating layer 431 sandwiched between the base layer 436 and a coating layer 433. The coating layer 433 may be a clear layer or can include a dye or some other material. The treatments shown in FIGS. 4A and 4B, when applied to regions of the AIOL outside the optical field of view, can be used to minimize dysphotopsia. When applied in such a fashion, the amount of stray light (either entering or reflected from the coated surfaces) entering the optical field of view is expected to be reduced or minimized.

Figure 5A:
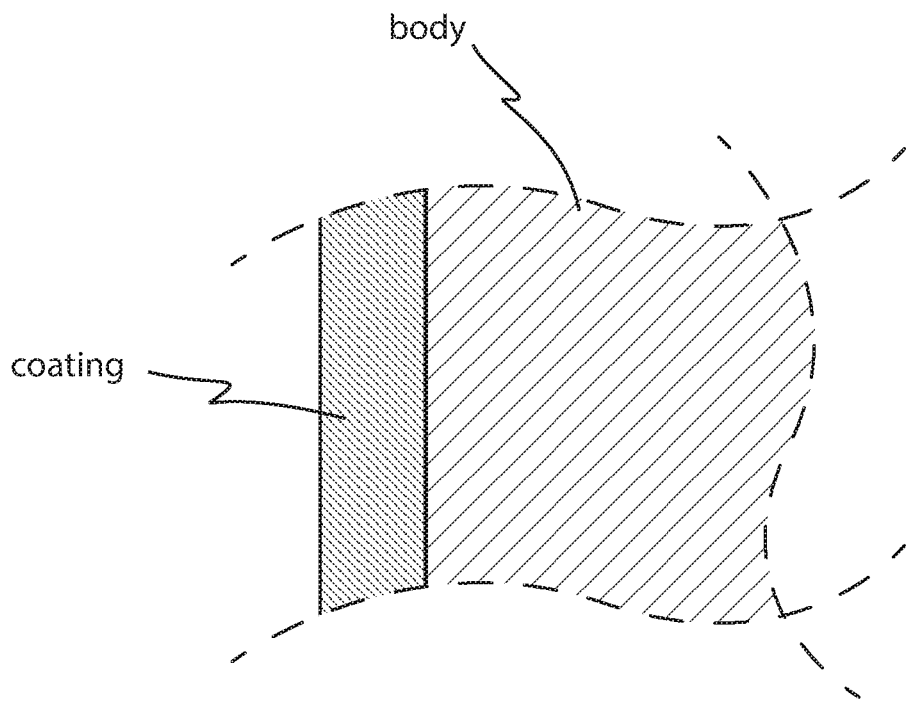
FIG. 5A shows a cross-sectional view of a surface treated portion of an accommodating lens structure configured in accordance with yet another embodiment of the present disclosure.
Figure 5B:
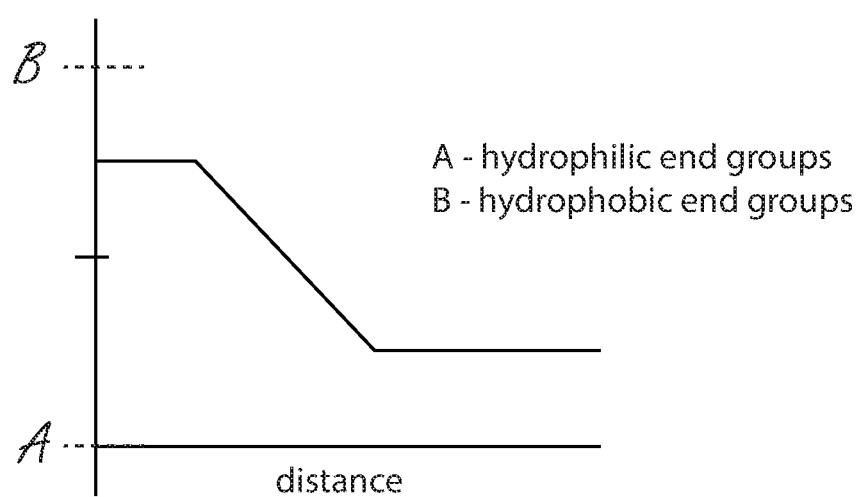
FIG. 5B graphically represents a relative surface energy associated with material at given depths through the cross section of FIG. 5A.

FIG. 5A illustrates an arbitrary cross section of a surface treated portion of an AIOL as described herein. The disclosed arrangement comprises a thin layer of coating material overlaying the body material. FIG. 5B graphically represents the relative surface energy associated with material at given depths through the cross section of FIG. 5A. The surface energy is described in terms proportion of hydrophilic end groups vs hydrophobic end groups. As best seen in FIG. 5B, the coating is more hydrophobic than the body material. As a result of the surface treatment process, there is a transition region within the body material in which addition hydrophobic end groups are incorporated indicated by the diagonal portion of the curve in FIG. 5B.

ADDITIONAL EXAMPLES

1. Coating composition
   a. Benz type formulations
   b. Fluro formulations
   c. Silanol coating
2. Coating methods
   a. Soak: almost all monomers
   b. Vapor deposition: Parylene
   c. Paint: thick monomers/viscous polymers
3. Coating initiation methods
   a. Thermal: Azobis and Esperox
   b. Photochemical: Azobis
4. High viscosity solutions
5. Coating expected outcomes
   a. Coating thickness
   b. Hydrophobicity of coatings
   c. Change surface texture
6. Measurements methods
   a. FTIR: ATR
   b. EDX: Auger
   c. Contact angles
7. Methods Example 1: Azobis Thermal Initiator A mixture containing xx gm of 2-HEMA, yy gm of EOEMA, zz gm of 2,2-azobis (2,4 dimethyl valeronitrile) and 0.3% by weight (of total mixture weight) of ethylene glycol dimethacrylate (EGDMA) were prepared in a clean vial. The mixture was thoroughly mixed using a magnetic stirrer making sure that there were no undissolved solid particles and there were no schlerian lines visible. The mixture was later filtered in a clean room through a 0.2 microns filter to remove any possible floating particles etc.

The samples of the lens parts to be coated were prepared. The side to be coated was exposed and other areas were protected from contact with the coating agents. The parts to be coated were dipped in the mixture from Table 1 for about 1-60 seconds and removed making sure that a film of the coating mixture was deposited. The lens was placed in an oven at 60° C. to cure for about 18 hours. Characterize by FTIR-ATR, contact angle(s) values and EDX.

The exact formulations with values of xx, yy, zz are shown in Table 1.

Example 2: UV Initiator

A mixture containing xx gm of 2-HEMA, yy gm of EOEMA, zz gm of 2,2-azobis (2,4 dimethyl valeronitrile) and 0.3% by weight (of total mixture weight) of ethylene glycol dimethacrylate (EGDMA) were prepared in a clean vial. The mixture was thoroughly mixed using a magnetic stirrer making sure that there were no undissolved solid particles and there were no schlerian lines visible. The mixture was later filtered in a clean room through a 0.2 microns filter to remove any possible floating particles, etc.

The samples of the lens parts to be coated were prepared. The side to be coated was exposed and all other areas were protected from contact with coating agents. The parts to be coated were dipped in the mixture from Table 1 for about 1-60 seconds and removed making sure that a film of the coating mixture was deposited. The lens was treated with a UV medium pressure mercury lamp with light emitting at a wavelength of >350 nm for about 2-6 minutes. The lamp was turned off and the parts were removed. Characterize by FTIR-ATR, contact angles values and EDX.

The exact formulations with values of xx, yy, zz are shown in Table 1.

TABLE 1

|   | HEMA (gm) | EGDMA (gm) | EOEMA (gm) | 2,2-azobis (2,4-dimethylvaleronitrile) (gm) |
|---|---|---|---|---|
| 1 | 9.76 | 0.22 | 21.53 | 0.05 |
| 2 | 20.38 | 0.11 | 10.33 | 0.05 |
| 3 | 9.11 | 0.84 | 20.09 | 0.05 |
| 4 | 19.81 | 0.42 | 10.05 | 0.05 |
| 5 | 16.71 | 0.36 | 13.78 | 0.05 |

Example 3: Esperox Thermal Initiator

A mixture containing xx gm of 2-HEMA, yy gm of EOEMA, zz gm of Esperox 33 (tert-Butyl peroxyneodecanoate, from Akzo Nobel Industries) and 0.3% by weight (of total mixture weight) of ethylene glycol dimethacrylate (EGDMA) were prepared in a clean vial. The mixture was thoroughly mixed using a magnetic stirrer making sure that there were no undissolved solid particles and there were no schlerian lines visible. The mixture was later filtered in a clean room through 0.2 microns filter to remove any possible floating particles etc.

The samples of the lens parts to be coated were prepared. The side to be coated was exposed and all other areas were protected from contact with the coating agents. The parts to be coated were dipped in the above mixture from Table 2 for about 1-60 seconds and removed making sure that a film of the coating mixture was deposited. The lens was placed in an oven at 40° C. to cure for about 18 hours. Characterize by FTIR-ATR, contact angle(s) values and EDX.

The exact formulations with values of xx, yy, zz are shown in Table 2 below.

TABLE 2

|   | HEMA (gm) | EGDMA (gm) | EOEMA (gm) | Esperox 33 (tert-Butyl peroxyneodecanoate) |
|---|---|---|---|---|
| 1 | 9.76 | 0.22 | 21.53 | 0.05 |
| 2 | 20.38 | 0.11 | 10.33 | 0.05 |
| 3 | 9.11 | 0.84 | 20.09 | 0.05 |
| 4 | 19.81 | 0.42 | 10.05 | 0.05 |
| 5 | 16.71 | 0.36 | 13.78 | 0.05 |

Example 4: UV Initiator

A mixture containing xx gm of 1,1,1,3,3,3-Hexafluoroisopropyl acrylate (gm), yy gm of Butyl acrylate (gm), and/or xy gm of 4-Hydroxybutyl acrylate (gm) zz gm of 2,2-azobis (2,4 dimethyl valeronitrile) and 0.3% by weight (of total mixture weight) of ethylene glycol dimethacrylate (EGDMA) was prepared in a clean vial. The mixture was thoroughly mixed using a magnetic stirrer making sure that there were no undissolved solid particles and there were no schlerian lines visible. The mixture was later filtered in a clean room through a 0.2 microns filter to remove any possible floating particles etc.

The samples of the lens parts to be coated were prepared. The side to be coated was exposed and all other areas were protected from contact with coating agents. The parts to be coated were dipped in the above mixture from Table 3 for about 1-60 seconds and removed making sure that a film of the coating mixture was deposited. The lens was treated with a UV medium pressure mercury lamp with light emitting at a wavelength of >350 nm for about 2-6 minutes. The lamp was turned off and the parts were removed. Characterize by FTIR-ATR, contact angle(s) values and EDX.

The exact formulations with values of xx, yy, xy, zz are shown in Table 3.

TABLE 3

|   | 1,1,1,3,3,3-Hexafluoroisopropyl acrylate (gm) | Butyl acrylate (gm) | 2,2-azobis (2,4-dimethylvaleronitrile) (gm) | 4-Hydroxybutyl acrylate (gm) | Ethylene glycol dimethacrylate (EGDMA) (gm) |
|---|---|---|---|---|---|
| 1 | 3.0000 | 1.7300 | 0.0032 | 0.0000 | 0.0144 |
| 2 | 3.0000 | 1.5300 | 0.0035 | 0.2300 | 0.0145 |
| 3 | 3.0000 | 2.1100 | 0.0034 | 0 | 0.0155 |

Example 5: Azobis Thermal Initiator

A mixture containing xx gm of 1,1,1,3,3,3-Hexafluoroisopropyl acrylate (gm), yy gm of Butyl acrylate (gm), and/or xy gm of 4-hydroxybutyl acrylate (gm) zz gm of 2,2-azobis (2,4 dimethyl valeronitrile) and 0.3% by weight (of total mixture weight) of ethylene glycol dimethacrylate (EGDMA) was prepared in a clean vial. The mixture was thoroughly mixed using a magnetic stirrer making sure that there were no undissolved solid particles and there were no schlerian lines visible. The mixture was later filtered in a clean room through 0.2 microns filter to remove any possible floating particles etc.

The samples of the lens parts to be coated were prepared. The side to be coated was exposed and all other areas were protected from contact with the coating agents. The parts to be coated were dipped in the above mixture from Table 3 for about 1-60 seconds and removed making sure that a film of the coating mixture was deposited. The lens was placed in an oven at 60° C. to cure for about 18 hours. Characterize by FTIR-ATR, contact angle(s) values and EDX.

The exact formulations with values of xx, yy, xy, zz are shown in Table 3.

Example 6: Esperox Thermal Initiator

A mixture containing xx gm of 1,1,1,3,3,3-Hexafluoroisopropyl acrylate (gm), yy gm of Butyl acrylate (gm), and/or xy gm of 4-hydroxybutyl acrylate (gm) zz gm of Esperox 33 (tert-Butyl peroxyneodecanoate) and 0.3% by weight (of total mixture weight) of ethylene glycol dimethacrylate (EGDMA) was prepared in a clean vial. The mixture was thoroughly mixed using a magnetic stirrer making sure that there were no undissolved solid particles and there were no schlerian lines visible. The mixture was later filtered in a clean room through 0.2 microns filter to remove any possible floating particles etc.

The samples of the lens parts to be coated were prepared. The side to be coated was exposed and all other areas were protected from contact with the coating agents. The parts to be coated were dipped in the above mixture from Table 3 for about 1-60 seconds and removed making sure that a film of the coating mixture was deposited. The lens was placed in an oven at 40° C. to cure for about 18 hours. Characterize by FTIR-ATR, contact angle(s) values and EDX.

The exact formulations with values of xx, yy, xy, zz are shown in Table 4.

TABLE 4

| | 1,1,1,3,3,3-Hexafluoroisopropyl acrylate (gm) | Butyl acrylate (gm) | Esperox 33 (tert-Butyl peroxyneodecanoate) (gm) | 4-Hydroxybutyl acrylate (gm) | Ethylene glycol dimethacrylate (EGDMA) (gm) |
|---|---|---|---|---|---|
| 1 | 3.0000 | 1.7300 | 0.0032 | 0.0000 | 0.0144 |
| 2 | 3.0000 | 1.5300 | 0.0035 | 0.2300 | 0.0145 |
| 3 | 3.0000 | 2.1100 | 0.0034 | 0 | 0.0155 |

Example 7: Siloxane Coating

A 95% ethanol in water solution was mixed with about 2 ml acetic acid and the pH was measured to be 4.5-5.5. The temperature was maintained to ambient (20° C.). The pH was adjusted if necessary to remain in the range of 4.5-5.5. A 2.0 ml solution of octyltriethoxysilane was measured in a hood and was added to the liquid slowly. The total time from the start of mixing the octyltriethoxysilane was 5 minutes.

In a separate process, the lens parts to be coated were prepared. The side to be coated was exposed and all other areas were protected from contact with coating agents. The parts to be coated were brought in contact with the above mixture for about 60-90 seconds. The parts were removed after 90 seconds and allowed to cure for about 24 hours at room temperature or 6-8 hours at 60° C. in an oven.

Characterize by FTIR-ATR, contact angle(s) values and EDX.

Example 8: Preparation of Thicker Coating Using UV Polymerization

A mixture containing xx gm of 2-HEMA, yy gm of EOEMA, zz gm of 2,2-azobis (2,4 dimethyl valeronitrile) and 0.3% by weight (of total mixture weight) of ethylene glycol dimethacrylate (EGDMA) was prepared in a clean vial per Table 1. The total volume of the mixture was adjusted to about 30 ml. The mixture was placed in a 40 ml glass vial. A magnetic stirrer was placed inside the mixture and was heated to 80-90° C. for about 8-10 minutes. The monomer solution was monitored closely. When the vortex created by the stir-bar completely disappeared (e.g. the surface of the liquid was completely flat), the monomer was removed quickly from the stir plate and was placed in the ice water. The monomer was agitated horizontally until it cooled completely.

The samples of the lens parts to be coated were prepared. The side to be coated was exposed and all other areas were protected from contact with the coating agents. The parts to be coated were dipped in the above mixture or the viscous solution was painted over it. The lens was treated with a UV medium pressure mercury lamp with light emitting at a wavelength of >350 nm for about 2-6 minutes. The lamp was turned off and the parts were removed.

Characterize by FTIR-ATR, contact angle(s) values and EDX.

The exact formulations with values of xx, yy, xy, zz are shown in Table 1.

Example 9: Preparation of Thicker Coating and Thermal Polymerization

A mixture containing xx gm of 2-HEMA, yy gm of EOEMA, zz gm of 2,2-azobis (2,4 dimethyl valeronitrile) and 0.3% by weight (of total mixture weight) of ethylene glycol dimethacrylate (EGDMA) was prepared in a clean vial per Table 1. The total volume of the mixture was adjusted to about 30 ml. The mixture was placed in a 40 ml glass vial. A magnetic stirrer was placed inside the mixture and was heated to 80-90° C. for about 8-10 minutes. The monomer solution was monitored closely. When the vortex created by the stir-bar completely disappeared (e.g. the surface of the liquid was completely flat), the monomer was removed quickly from the stir plate and was placed in the ice water. The monomer was agitated horizontally until it cooled completely.

The samples of the lens parts to be coated were prepared. The side to be coated was exposed and all other areas were protected from contact with coating agents. The parts to be coated were dipped in the above mixture or the viscous solution was painted over it. The coated parts were placed at 60° C. in an oven for a minimum of 18 hours.

Characterize by FTIR-ATR, contact angle(s) values and EDX.

The exact formulations with values of xx, yy, zz are shown in Table 1.

Example 10: Preparation of Thicker Coating and Esperox 33 Polymerization

A mixture containing xx gm of 2-HEMA, yy gm of EOEMA, zz gm of Esperox 33 (tert-Butyl peroxyneodecanoate and 0.3% by weight (of total mixture weight) of ethylene glycol dimethacrylate (EGDMA) was prepared in a clean vial per Table 1. The total volume of the mixture was adjusted to about 30 ml. The mixture was placed in a 40 ml glass vial. A magnetic stirrer was placed inside the mixture and was heated to 80-90° C. for about 8-10 minutes. The monomer solution was monitored closely. When the vortex created by the stir-bar completely disappeared (e.g. the surface of the liquid was completely flat), the monomer was removed quickly from the stir plate and was placed in the ice water. The monomer was agitated horizontally until it cooled completely.

The samples of the lens parts to be coated were prepared. The side to be coated was exposed and all other areas were protected from contact with the coating agents. The parts to be coated were dipped in the above mixture or the viscous solution was painted over it. The coated parts were placed at 40° C. in an oven for a minimum of 18 hours.

Characterize by FTIR-ATR, contact angle(s) values and EDX.

The exact formulations with values of xx, yy, zz are shown in Table 2.

Example 11: Parylene Coating

The samples of the lens parts to be coated were prepared. The side to be coated was exposed and all other areas were protected from contact with coating agents. The coating was applied at a vendor site. Basically, the solid dimer was heated under vacuum and vaporized into a dimeric gas. The gas was then pyrolyzed to cleave the dimer to its monomeric form.

In the room temperature deposition chamber, the monomer gas was deposited on all surfaces as a thin, transparent polymer film.

Characterize by FTIR-ATR, contact angle(s) values and EDX.

Example 12: UV Initiator

A mixture containing xx gm of 2-HEMA, yy gm of EOEMA, zz gm of 2,2-azobis (2,4 dimethyl valeronitrile) and 0.3% by weight (of total mixture weight) of ethylene glycol dimethacrylate (EGDMA) were prepared in a clean vial. The mixture was thoroughly mixed using a magnetic stirrer making sure that there were no undissolved solid particles and there were no schlerian lines visible. The mixture is heated (at 90° C.) and stirred to form oligomers. The process is terminated when the viscosity is at a selected level (e.g., approximately 150-250 cps, approximately 200 cps), and the mixture is then cooled to stop the reaction. The resulting mixture is then stored for use.

The mixture can be dispensed on selected surface(s) for treatment via a digital syringe or any of the methods disclosed herein. The treated surfaces are post treated by allowing them to sit for 30 minutes at room temperature, and then at 40° C. for 18 hours under argon.

Features Key—Figures

Below are the key codes for the features specified in the figures described herein. Particular figure features are numbered using the figure number preceding one of the codes listed below. For example, the feature number for the AIOL of FIG. 1 is 100. Subsets of a feature may also receive an alpha designator at the end of the feature number, for example the bellows region 140 may be comprised of a first and second bellows region, designated as 140a and 140b, respectively.

| Feature Description | Feature Code |
|---|---|
| AIOL | 00 |
| coated surface | 01 |
| uncoated surface | 02 |
| outer surface | 03 |
| seam/bond joint | 04 |
| seam/bond joint | 05 |
| seam/bond joint | 06 |
| masked regions | 07 |
| cross section | 08 |
| machined surface | 09 |
| first component | 10 |
| inner surface | 11 |
| fluid accommodating lens | 12 |
| outer surface | 13 |
| second component | 20 |
| inner surface | 21 |
| outer surface | 23 |
| fluid chamber | 30 |
| attenuating layer | 31 |
| first optical components | 32 |
| coating layer | 33 |
| second optical components | 34 |
| AIOL structure | 35 |
| base layer | 36 |
| bellows region | 40 |
| fixed lens assembly | 50 |
| optical portion | 51 |
| passages | 52 |
| continuous thickened region | 53 |
| fixed lens inner surface | 54 |
| engagement feature | 55 |
| fluid accommodating lens | 60 |

EXAMPLES

Several aspects of the present technology are set forth in the following examples.

1. An accommodating intraocular lens system, comprising:
    an accommodating structure including a first component, a second component posterior of the first optical component, an inner fluid chamber between the first and second optical components, and an outer fluid chamber fluidically coupled to the inner fluid chamber,
    wherein the first component and the second component are hydrophilic structures, and wherein one or more surfaces of the accommodating structure include a surface treatment to decrease a roughness of the corresponding treated region.

2. The accommodating intraocular lens system of example 1 wherein the treated surfaces comprise the same proportion of hydrophobic and hydrophilic elements as the base material.

3. The accommodating intraocular lens system of example 1 wherein the treated surfaces comprise a proportion of approximately 25% 2-Hydroxyethyl methacrylate (HEMA) elements to approximately 75% hydrophobic elements.

4. The accommodating intraocular lens system of any one of examples 1-3 wherein an inner surface defining, at least in part, the inner fluid chamber includes the surface treatment.

5. The accommodating intraocular lens system of any one of examples 1-4 wherein the accommodating structure comprises an outer surface defined, at least in part, by a periphery of the first component and the second component, and wherein at least a portion of the outer surface includes the surface treatment.

6. The accommodating intraocular lens system of any one of examples 1-5 wherein the surface treatment comprises a coating applied to the corresponding one or more surfaces of the accommodating structure.

7. The accommodating intraocular lens system of example 1 wherein the surface treatment is adapted to reduce the density of hydrophilic end groups from the treated region.

8. The accommodating intraocular lens system of example 1 wherein the surface treatment is adapted to mask hydrophilic end groups from the treated region.

9. The accommodating intraocular lens system of any one of examples 1-8 wherein the outer fluid chamber is around at least a portion of the inner fluid chamber and configured to interface with a native eye capsule of a human subject such that fluid flows between the outer fluid chamber and the inner fluid chamber to move the first optical element for providing accommodation.

10. The accommodating intraocular lens system of any one of examples 1-9, further comprising fluid within the inner fluid chamber, wherein the fluid comprises a hydrophobic liquid.

11. The accommodating intraocular lens system of any one of examples 1-10 wherein the first and second components are bonded to one another.

12. The accommodating intraocular lens system of any one of examples 1-11 wherein the first and second components are bonded to one another at one or more bond sites, and wherein the one or more bond sites do not include the surface treatment.

13. The accommodating intraocular lens system of any one of examples 1-12 wherein the first and second components are sufficiently flexible to be folded into a reduced cross-section delivery configuration.

14. An accommodating intraocular lens system for implantation within a lens capsule of a subject, comprising:
an accommodating structure including a first optical component and a second optical component coupled to the first optical component along a boundary surface, an inner fluid chamber between the first and second optical components, and an outer fluid chamber fluidically coupled to the inner fluid chamber;
wherein the accommodating structure comprises a substantially hydrophilic outer surface and a substantially hydrophobic inner surface as defined by inner fluid chamber and the outer fluid chamber,
a coating on at least one of the first optical component and the second optical component, wherein the coating changes hydrophobicity of the treated regions as compared to untreated regions of the first and second optical components.

15. The accommodating intraocular lens system of example 14 wherein the hydrophilic outer surface of the accommodating structure is composed of a first material, and wherein the coating comprises a prepolymer of the first material.

16. The accommodating intraocular lens system of example 15 wherein first material comprises a copolymer of 2-Hydroxyethyl methacrylate (HEMA) and 2-Ethoxyethyl methacrylate (EOEMA)

17. The accommodating intraocular lens system of example 15 wherein the coating comprises EOEMA.

18. The accommodating intraocular lens system of any one of examples 14-17 wherein the coating reduces surface roughness of the treated regions as compared with untreated regions of the first and second optical components.

19. The accommodating intraocular lens system of example 14 wherein the coating increases hydrophobicity of the treated regions as compared to untreated regions.

20. An accommodating intraocular lens for placement within a lens capsule of a subject, the accommodating intraocular lens comprising:
a first component having a first optical region and a first bellows region;
a second component having a second optical region and a second bellows region, the second component coupled to the first component;
a first fluid chamber between the first optical region and the second optical region;
a second fluid chamber between the first bellows region and the second bellows region, the second fluid chamber in fluid communication with the first fluid chamber to transfer fluid between the first fluid chamber and the second fluid chamber in response to shape changes of the lens capsule to provide optical power changes to the accommodating intraocular lens; and
a surface treatment applied to a first treated region of the first component and a second treated region of the second component, wherein the surface treatment increases the hydrophobicity of the corresponding first and second treated regions.

21. An accommodating intraocular lens for placement within a lens capsule of a subject, the accommodating intraocular lens comprising a generally hydrophilic surface, and wherein the accommodating intraocular lens includes a coating on at least a portion of the surface, and further wherein the coated regions of the surface of the accommodating intraocular lens are more hydrophobic than untreated regions of the surface.

CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, any of the features of the intraocular lens systems described herein may be combined with any of the features of the other intraocular lenses described herein and vice versa. Moreover, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An accommodating intraocular lens system, comprising:
   an accommodating structure including a first component, a second component posterior of the first component, an inner fluid chamber between the first and second components, and an outer fluid chamber fluidically coupled to the inner fluid chamber,
   wherein the first component and the second component are hydrophilic structures, and wherein one or more surfaces of the accommodating structure include a surface treatment to decrease a surface roughness of a region treated with the surface treatment; and
   wherein the one or more surfaces of the accommodating structure including the surface treatment comprise a proportion of approximately 25% 2-Hydroxyethyl methacrylate (HEMA) elements to approximately 75% hydrophobic elements.

2. The accommodating intraocular lens system of claim 1 wherein the regions of the one or more surface of the accommodating structure treated with the surface treatment comprise a same proportion of hydrophobic and hydrophilic elements as a base material.

3. The accommodating intraocular lens system of claim 1 wherein an inner surface defining, at least in part, the inner fluid chamber includes the surface treatment.

4. The accommodating intraocular lens system of claim 1 wherein the accommodating structure comprises an outer surface defined, at least in part, by a periphery of the first component and the second component, and wherein at least a portion of the outer surface includes the surface treatment.

5. The accommodating intraocular lens system of claim 1 wherein the surface treatment comprises a coating applied to the corresponding one or more surfaces of the accommodating structure.

6. The accommodating intraocular lens system of claim 1 wherein the surface treatment is adapted to reduce the density of hydrophilic end groups within the treated region.

7. The accommodating intraocular lens system of claim 1 wherein the surface treatment is adapted to mask hydrophilic end groups within the treated region.

8. The accommodating intraocular lens system of claim 1 wherein the outer fluid chamber is around at least a portion of the inner fluid chamber and configured to interface with a native eye capsule of a human subject such that fluid flows between the outer fluid chamber and the inner fluid chamber to move the first optical element for providing accommodation.

9. The accommodating intraocular lens system of claim 1, further comprising fluid within the inner fluid chamber, wherein the fluid comprises a hydrophobic liquid.

10. The accommodating intraocular lens system of claim 1 wherein the first and second components are bonded to one another.

11. The accommodating intraocular lens system of claim 10 wherein the first and second components are bonded to one another at one or more bond sites, and wherein the one or more bond sites do not include the surface treatment.

12. The accommodating intraocular lens system of claim 1 wherein the first and second components are sufficiently flexible to be folded into a reduced cross-section delivery configuration.

13. An accommodating intraocular lens system for implantation within a lens capsule of a subject, comprising:
    an accommodating structure including a first optical component and a second optical component coupled to the first optical component along a boundary surface, an inner fluid chamber between the first and second optical components, and an outer fluid chamber fluidically coupled to the inner fluid chamber;
    wherein the accommodating structure comprises a hydrophilic outer surface and a hydrophobic inner surface as defined by the inner fluid chamber and the outer fluid chamber,
    a coating on at least one of the first optical component and the second optical component, wherein the coating changes hydrophobicity of the treated regions as compared to untreated regions of the first and second optical components;
    wherein the hydrophilic outer surface of the accommodating structure is composed of a first material, and wherein the coating comprises a prepolymer of the first material.

14. The accommodating intraocular lens system of claim 13 wherein the first material comprises a copolymer of 2-Hydroxyethyl methacrylate (HEMA) and 2-Ethoxyethyl methacrylate (EOEMA).

15. The accommodating intraocular lens system of claim 13 wherein the coating comprises 2-Ethoxyethyl methacrylate (EOEMA).

16. The accommodating intraocular lens system of claim 13 wherein the coating reduces surface roughness of the treated regions as compared with untreated regions of the first and second optical components.

17. The accommodating intraocular lens system of claim 13 wherein the coating increases hydrophobicity of the treated regions as compared to untreated regions.

* * * * *